(12) United States Patent
Hill

(10) Patent No.: US 7,345,771 B2
(45) Date of Patent: Mar. 18, 2008

(54) APPARATUS AND METHOD FOR MEASUREMENT OF CRITICAL DIMENSIONS OF FEATURES AND DETECTION OF DEFECTS IN UV, VUV, AND EUV LITHOGRAPHY MASKS

(75) Inventor: Henry Allen Hill, Tucson, AZ (US)

(73) Assignee: Zetetic Institute, Tucson, AZ (US)

(*) Notice: Subject to any disclaimer, the term of this patent is extended or adjusted under 35 U.S.C. 154(b) by 0 days.

(21) Appl. No.: 11/124,603

(22) Filed: May 6, 2005

(65) Prior Publication Data

US 2005/0254063 A1    Nov. 17, 2005

Related U.S. Application Data

(60) Provisional application No. 60/571,967, filed on May 18, 2004, provisional application No. 60/569,807, filed on May 11, 2004, provisional application No. 60/568,774, filed on May 6, 2004.

(51) Int. Cl.
*G01B 11/02* (2006.01)

(52) U.S. Cl. .................. 356/496; 356/516

(58) Field of Classification Search .......... 356/450, 356/489, 495, 496, 511, 512, 516, 521, 498
See application file for complete search history.

(56) References Cited

U.S. PATENT DOCUMENTS

| | | |
|---|---|---|
| 3,628,027 A | 12/1971 | Brauss |
| 3,748,015 A | 7/1973 | Offner |
| 4,011,011 A | 3/1977 | Hemstreet et al. |
| 4,226,501 A | 10/1980 | Shafer |
| 4,272,684 A | 6/1981 | Seachman |
| 4,685,803 A | 8/1987 | Sommargren |
| 4,733,967 A | 3/1988 | Sommargren |
| 5,220,403 A | 6/1993 | Batchelder |
| 5,241,423 A | 8/1993 | Chiu et al. |
| 5,327,223 A | 7/1994 | Korth |
| 5,485,317 A | 1/1996 | Perissinotto |
| 5,602,643 A | 2/1997 | Barrett |
| 5,614,763 A | 3/1997 | Womack |
| 5,633,972 A | 5/1997 | Walt |
| 5,659,420 A | 8/1997 | Wakai |
| 5,699,201 A | 12/1997 | Lee |
| 5,757,493 A | 5/1998 | Vankerkhove |
| 5,760,901 A | 6/1998 | Hill |
| 5,828,455 A | 10/1998 | Smith |
| 5,883,714 A * | 3/1999 | Jann et al. ............ 356/484 |

(Continued)

OTHER PUBLICATIONS

U.S. Appl. No. 09/852,369, filed Jan. 3, 2002, Hill.

(Continued)

*Primary Examiner*—Tarifur Chowdhury
*Assistant Examiner*—Jonathan M Hansen
(74) *Attorney, Agent, or Firm*—Wilmer Cutler Pickering Hale & Dorr LLP

(57) ABSTRACT

Methods and apparatus are disclosed for measurement of critical dimensions (CD) of features and detection of defects in reflecting UV, VUV, and EUV lithography masks and in transmitting UV and VUV lithography masks. The measured CD's may be used in the determination of optical proximity corrections (OPC) and/or in mask fabrication process control. The transmitting masks may comprise binary and various types of phase shift masks.

39 Claims, 21 Drawing Sheets

U.S. PATENT DOCUMENTS

| | | | |
|---|---|---|---|
| 5,894,195 | A | 4/1999 | McDermott |
| 5,915,048 | A | 6/1999 | Hill et al. |
| 6,011,654 | A | 1/2000 | Schweizer Juergen et al. |
| 6,052,231 | A | 4/2000 | Rosenbluth |
| 6,091,496 | A | 7/2000 | Hill |
| 6,124,931 | A | 9/2000 | Hill |
| 6,271,923 | B1 | 8/2001 | Hill |
| 6,330,065 | B1 | 12/2001 | Hill |
| 6,445,453 | B1 | 9/2002 | Hill |
| 6,447,122 | B1 | 9/2002 | Kobayashi et al. |
| 6,480,285 | B1 | 11/2002 | Hill |
| 6,552,805 | B2 | 4/2003 | Hill |
| 6,552,852 | B2 | 4/2003 | Hill |
| 6,597,721 | B1 | 7/2003 | Hutchinson et al. |
| 6,606,159 | B1 | 8/2003 | Hill |
| 6,667,809 | B2 | 12/2003 | Hill |
| 6,714,349 | B2 | 3/2004 | Nam |
| 6,717,736 | B1 | 4/2004 | Hill |
| 6,753,968 | B2 | 6/2004 | Hill |
| 6,775,009 | B2 | 8/2004 | Hill |
| 6,847,029 | B2 | 1/2005 | Hill |
| 6,847,452 | B2 | 1/2005 | Hill |
| 2002/0074493 | A1 | 6/2002 | Hill |
| 2002/0131179 | A1 | 9/2002 | Hill |
| 2003/0174992 | A1 | 9/2003 | Levene |
| 2004/0201852 | A1 | 10/2004 | Hill |
| 2004/0201853 | A1 | 10/2004 | Hill |
| 2004/0201854 | A1 | 10/2004 | Hill |
| 2004/0201855 | A1 | 10/2004 | Hill |
| 2004/0202426 | A1 | 10/2004 | Hill |
| 2004/0227950 | A1 | 11/2004 | Hill |
| 2004/0227951 | A1 | 11/2004 | Hill |
| 2004/0228008 | A1 | 11/2004 | Hill |
| 2004/0246486 | A1 | 12/2004 | Hill |
| 2004/0257577 | A1 | 12/2004 | Hill |
| 2005/0036149 | A1 | 2/2005 | Hill |

OTHER PUBLICATIONS

U.S. Appl. No. 09/917,402, filed Jul. 27, 2001, Hill.
U.S. Appl. No. 10/765,254, filed Jan. 27, 2004, Hill.
U.S. Appl. No. 10/765,368, filed Jan. 27, 2004, Hill.
U.S. Appl. No. 10/886,157, filed Jul. 7, 2004, Hill.
U.S. Appl. No. 60/442,858, filed Jul. 27, 2002, Hill.
U.S. Appl. No. 60/442,982, filed Jan. 29, 2003, Hill.
U.S. Appl. No. 60/443,980, filed Jan. 31, 2003, Hill.
U.S. Appl. No. 60/444,707, filed Jan. 4, 2003, Hill.
U.S. Appl. No. 60/445,739, filed Feb. 7, 2003, Hill.
U.S. Appl. No. 60/447,254, filed Feb. 13, 2003, Hill.
U.S. Appl. No. 60/448,250, filed Jan. 19, 2003, Hill.
U.S. Appl. No. 60/448,360, filed Feb. 19, 2003, Hill.
U.S. Appl. No. 60/459,425, filed Apr. 11, 2003, Hill.
U.S. Appl. No. 60/459,493, filed Apr. 1, 2003, Hill.
U.S. Appl. No. 60/460,129, filed Apr. 3, 2003, Hill.
U.S. Appl. No. 60/485,255, filed Jul. 7, 2003, Hill.
U.S. Appl. No. 60/485,507, filed Jul. 7, 2003, Hill.
U.S. Appl. No. 60/501,666, filed Sep. 10, 2003, Hill.
U.S. Appl. No. 60/506,715, filed Sep. 26, 2003, Hill.

* cited by examiner

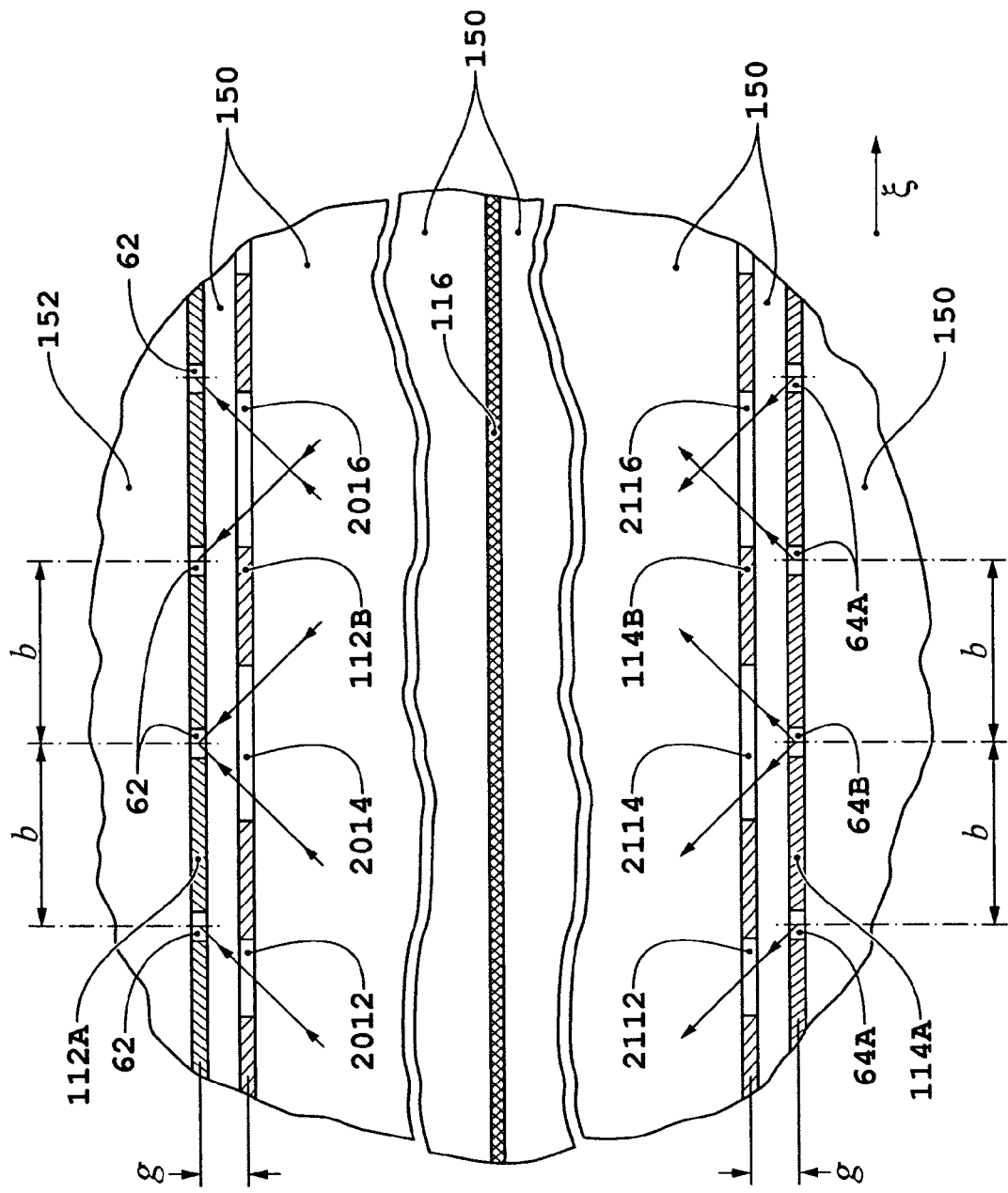

APPARATUS AND METHOD FOR MEASUREMENT OF CRITICAL DIMENSIONS OF FEATURES AND DETECTION OF DEFECTS IN UV, VUV, AND EUV LITHOGRAPHY MASKS

This application claims the benefit of U.S. Provisional Application No. 60/568,774, filed May 6, 2004; U.S. Provisional Application No. 60/569,807, filed May 11, 2004; and U.S. Provisional Application No. 60/571,967, filed May 18, 2004, all of which are incorporated herein by reference.

TECHNICAL FIELD

This invention is generally in the field of manufacturing of multi-layer structures, such as semiconductor wafers and ICs, and relates to measuring location of alignment marks, defects on wafers and masks, and CDs of pattern features through the use of displacement interferometric metrology systems and interferometric imaging metrology systems operating in the IR to VUV and EUV and the use of measured properties of reflected/scattered fields in the IR to VUV and EUV by patterned wafers.

RELATED APPLICATIONS

The following patent applications are related to the present application: U.S. patent application No.: 10/778,371, filed Feb. 13, 2004, entitled "Transverse Differential Interferometric Confocal Microscopy," (ZI-40); Ser. No. 10/782,057, filed Feb. 19, 2004, entitled "Longitudinal Differential Interferometric Confocal Microscopy for Surface Profiling," (ZI-41); Ser. No. 10/782,058, filed Feb. 19, 2004, entitled "Method and Apparatus for Dark Field Interferometric Confocal Microscopy," (ZI-42); Ser. No. 10/765,254, filed Jan. 27, 2004, entitled "Leaky Guided Wave Modes Used in Interferometric Confocal Microscopy to Measure Properties of Trenches," (ZI-46); Ser. No. 10/816,180, filed Apr. 1, 2004, entitled "Apparatus and Method for Joint Measurement Of Fields Of Scattered/Reflected or Transmitted Orthogonally Polarized Beams By An Object In Interferometry," (ZI-50); Ser. No. 10/816,172, filed Apr. 1, 2004, entitled "Apparatus and Method for Measurement Of Backscattered and Forward Scattered/Reflected By An Object In Interferometry," (ZI-51); Ser. No. 10/886,010, filed Jul. 7, 2004, entitled "Apparatus And Method For High Speed Scan For Sub-Wavelength Defects And Artifacts In Semiconductor Metrology," (ZI-52); No. 60/568,774, filed May 6, 2004, entitled "Apparatus And Methods For Measurement Of Critical Dimensions Of Features And Detection Of Defects In UV, VUV, And EUV Lithography Masks," (ZI-60); No. 60/569,807, filed May 11, 2004, entitled "Apparatus And Methods For Measurement Of Critical Dimensions Of Features And Detection Of Defects In UV, VUV, And EUV Lithography Masks," (ZI-61); and No. 60/571,967, filed May 18, 2003, entitled "Apparatus And Methods For Measurement Of Critical Dimensions Of Features And Detection Of Defects In UV, VUV, And EUV Lithography Masks," (ZI-63).

BACKGROUND OF THE INVENTION

There are known techniques for measuring CD's using a scanning electron microscope (CD-SEM); a scanning probe microscope (CD-SPM) such as described in commonly owned U.S. Pat. No. 6,445,453 (ZI-14) entitled "Scanning Interferometric Near-Field Confocal Microscopy" by Henry A. Hill, the contents of which are herein incorporated in their entirety by reference; and a scanning optical microscopy (CD-SOM) based on images of features. There are also known techniques for measuring the profile of a surface by the use of different forms of linear displacement interferometric metrology such as based on white light interferometric techniques and there are known techniques for measuring properties of a surface for example using differential confocal microscopy.

SUMMARY OF THE INVENTION

Information obtained by at least some of the herein-described processes regarding the transverse position of features is based on relative phase measurements and not on the analysis of distributions of intensities or of amplitudes in an image plane. Also, in at least some of the practices taught herein, information about the CD's of features is based on differential phase and amplitude measurements and not on the analysis of distributions of intensities or of amplitudes in an image plane. It is for these reasons in part that a detailed knowledge is not required of the scattering properties of features in the practice of at least some of the embodiments described herein.

A further consequence of at least some of the embodiments described herein being based on relative phase measurements is that the measurement of relative distances between features having the same or similar composition with respect to indices of refraction is to a high level independent of knowledge of optical properties of those portions of a measurement object responsible for generation of the measured reflected/scattered fields.

At least some of the methods and apparatus described herein are used for the measurement of CD's of features and the detection of defects in reflecting UV, VUV, and EUV lithography masks and in transmitting UV and VUV lithography masks. An error in a CD of a feature is measured and/or a defect is detected and/or properties thereof measured using linear displacement interferometric metrology and differential interferometric confocal and non-confocal microscopy. The defects may be in the form of an error in the profile of a horizontal or vertical surface or in the form of a particle on an open surface, in an open feature, or embedded in an interior portion of a mask. Defects in any one of external or interior surfaces, reflecting substrate, buffers, phase shifters, and absorbers of a mask may also be detected at different times during the fabrication of the mask by use of the linear displacement interferometric metrologies and the differential interferometric confocal and non-confocal microscopy.

Defects and/or CD's in a patterned absorber may be measured before the etching of the pattern into an adjacent layer, e.g., a buffer, by use of the linear displacement interferometric metrologies and the differential interferometric confocal and non-confocal microscopy. The CD of an absorber section of a feature and the CD of a corresponding buffer section of the feature may each be measured by using different polarization states of measurement beams in the linear displacement interferometric metrologies and the differential interferometric confocal and non-confocal microscopy.

The calibration of the CD measurement scale is traceable to independently calibrated standards. The interferometric metrologies and the differential interferometric confocal and non-confocal microscopy may use bi- or quad-homodyne detection techniques or variants thereof to obtain joint measurements of arrays of conjugated quadratures of fields reflected/or scattered by defects and/or features in a mask. Elements of arrays of the conjugated quadratures are measured simultaneously leading to advantages of reduced sensitivity to vibrations and to a high throughput.

In addition, information about the properties of a defect with respect to the real and complex components n and k, respectively, of the refractive index may be obtained using different polarization states and/or wavelengths of measurement beams in the interferometric metrologies.

The procedures described herein require general knowledge of the feature geometry of masks. However, the procedures generally do not require detailed knowledge of the properties of the fields reflected/scattered by the features of a reference or standard mask, e.g., angular distributions of reflected/scattered measurement beams or phase shifts introduced by reflections/scattering of measurement beams, wherein the reference or standard mask is one that meets requirements with respect to presence of defects and to values of CD's.

The lateral resolution used in defect detection and in detection of CD errors can be matched respectively to the typical size of defects so as to maximize the respective detection efficiency and be matched to dimensions of subsections of features that is optimum for use of CD errors in OPC analysis. The precision to which CD's are measured can be sub-nanometer, the profile of a surface can be measured to an accuracy of the order of 0.1 nm for a UV measurement beam with corresponding accuracies for visible, VUV, and EUV measurement beams, and the mean size of particle defects detected and the size of dimensions of the subsections of features measured may be of the order of 35 nm for a VUV measurement beam with corresponding dimensions for visible, UV, and EUV measurement beams. The corresponding properties for the other cited wavelength measurement beams generally scale with the wavelength of the measurement beam.

UV and VUV measurement beams can be used effectively for detecting defects and of errors in CD's in UV, VUV, and EUV masks for the technology nodes of hp65 nm, hp45 nm, hp32 nm, and hp22 nm nodes as set out in the International Technology Roadmap for Semiconductors (ITRS), 2003 Edition because of the typical magnification of 4 or 5 present in lithography tools between the object plane at the mask or reticle stage and the image plane at the wafer stage. The height of walls of features in the corresponding mask is of the order of 100 to 150 nm determined by the transmitting properties of absorbing and buffer media, the amplitude of phase shifts in phase shifting masks, and exposure wavelength of a given lithography tool.

The CD of an absorbing layer portion of a feature relative to the CD of a buffer layer portion of the feature can be measured by use of s and p polarization states of measurement beams incident on the feature because the reflecting properties of the absorber and the buffer have significantly different dependences on the polarization state of the measurement beam.

In general, in one aspect, the invention features an interferometry system for examining a surface of an object. The system includes: a source assembly that generates a measurement beam; a detector assembly that includes a detector element; an interferometer that includes a source imaging system that focuses the measurement beam onto a spot on the surface of the object and an object imaging system that images the spot onto the detector element as an interference beam to generate an interference signal therefrom, the object imaging system combining a return measurement beam coming from the spot with a reference beam to produce the interference beam, wherein the measurement beam upon interaction with the surface of the object produces a backscattered component and a forward-scattered component; and a processor programmed to determine oblique angle-of-incidence information about a feature or defect on the surface of the object by using the backscattered component but not the forward scattered component.

In general, in another aspect, the invention features an interferometry system for examining a surface of an object. In this case, system includes: a source assembly that generates a measurement beam; a detector assembly that includes a detector element; and an interferometer that includes a source imaging system that focuses the measurement beam onto a spot on the surface of the object and an object imaging system that images the spot onto the detector element as an interference beam to generate an interference signal therefrom, the object imaging system combining a return measurement beam coming from the spot with a reference beam to produce the interference beam, wherein the source imaging system causes the measurement beam that arrives at the surface of the object to have an average angle of incidence that is oblique to the surface of object, wherein the measurement beam upon interaction with the surface of the object produces a backscattered component and a forward-scattered component, and wherein the object imaging system is configured to collect the backscattered component but not the forward scattered component to generate the return measurement beam.

Embodiments have one or more of the following features. The source imaging system generates the measurement beam such that it has an angle of incidence relative to the surface of the object that ranges between $\theta_1$ and $\theta_2$, wherein $\theta_1$ and $\theta_2$ are angles that are less than 90° and wherein $\theta_1 < \theta_2$. The interferometer is a linear displacement interferometer, more specifically, a scanning, linear displacement interferometer. The interferometry system also includes a catadioptric imaging system that implements at least part of both the source imaging system and the object imaging system.

In general, in yet another aspect, the invention features an interferometry system for examining a surface of an object, wherein the system includes: a source assembly that generates an array of measurement beams; a detector assembly that includes an array of detector elements; an interferometer that includes a source imaging system that focuses the array of measurement beams onto an array of spots on the object and an object imaging system that images the array of spots onto the array of detector elements as an array of interference beams, the object imaging system combining an array of return measurement beams coming from the array of spots with an array of reference beams to produce the array of interference beams, wherein the array of measurement beams upon interaction with the surface of the object produces an array of backscattered components and an array of forward-scattered components; and a processor programmed to determine oblique angle-of-incidence information about features or defects on the surface of the object by using the array of backscattered components but not the array of forward scattered components.

In general, in still another aspect, the invention features an interferometry system for examining a surface of an object that includes: a source assembly that generates an array of measurement beams; a detector assembly that includes an array of detector elements; and an interferometer that includes a source imaging system that focuses the array of measurement beams onto an array of spots on the object and an object imaging system that images the array of spots onto the array of detector elements as an array of interference beams, the object imaging system combining an array of return measurement beams coming from the array of spots with an array of reference beams to produce the array of interference beams, wherein the source imaging system causes the array of measurement beams to arrive at the surface along a range of directions that is characterized by an average angle of incidence that is oblique to the surface of the object, wherein the array of measurement beams upon interaction with the surface of the object produces an array of backscattered components and an array of forward-scattered components and wherein the object imaging system uses the array of backscattered components but not the array of forward scattered components to generate the array of return measurement beams.

Other embodiments include one or more of the following features. The source imaging system generates the measurement beam array such that it has an angle of incidence relative to the surface of the object that ranges between $\theta_1$ and $\theta_2$, wherein $\theta_1$ and $\theta_2$ are angles that are less than 90° and wherein $\theta_1 < \theta_2$. The interferometer is a linear displacement interferometer, more specifically, a scanning, linear displacement interferometer. The interferometry system also includes a catadioptric imaging system that implements at least part of both the source imaging system and the object imaging system. The source assembly includes an optical component that simultaneously generates a first, a second, and a third array of measurement beams, wherein the first array of measurement beams is the first-mentioned array of measurement beams, wherein the source imaging system focuses the second array of measurement beams onto the surface along a second range of directions characterized by an average angle of incidence that is oblique to the surface of the object, the second direction being different from the first-mentioned direction, and wherein the source imaging system focuses the third array of measurement beams onto the surface so that the third array of measurement beams arrives at the surface of the object with an average angle of incidence that is non-oblique relative to the surface of the object. The source imaging system images the second array of measurement beams onto a second array of spots on the object and images the third array of measurement beams onto a third array of spots on the object, wherein the first, second, and third arrays of spots are distinct from each other. The first and second directions are complimentary to each other. The optical component includes a pinhole array beam splitter and a spatial filter.

In general, in still yet another aspect, the invention features a method of interferometrically examining a surface of an object. The method involves: generating a measurement beam; focusing the measurement beam onto a spot on the surface of the object wherein upon interaction with the surface of the object the measurement beam produces a backscattered component and a forward-scattered component; combining a return measurement beam from the object with a reference beam to generate an interference beam; generating an interference signal from the interference beam; and from the interference signal, determining oblique angle-of-incidence information about a feature or defect on the surface of the object, wherein determining involves using the backscattered component but not the forward scattered component.

Other embodiments include one or more of the following features. The method also involves collecting the backscattered component from the surface of the object but not the forward scattered component to generate the return measurement beam. The method also involves interferometrically determining height profile information about the surface of the object and then using both the height profile information and the oblique angle-of-incidence information to determine locations of features on the surface of the object.

In general, in still yet another aspect, the invention features another method of interferometrically examining a surface of an object. The method involves: generating an array of measurement beams; focusing the array of measurement beams onto an array of spots on the object, wherein upon interacting with the surface of the object the array of measurement beams produces an array of backscattered components and an array of forward-scattered components; combining an array of return measurement beams from the object with an array of reference beams to generate an array of interference beams; generating an array of interference signals form the array of interference beams; from the array of interference signals, determining oblique angle-of-incidence information about a feature or defect on the surface of the object, wherein determining involves using the array of backscattered components but not the array forward scattered components.

Other embodiments include one or more of the following features. Focusing the first-mentioned array of measurement beams onto the object involves delivering the first-mentioned array of measurement beams onto the object along a first range of directions characterized by an average angle of incidence that is oblique to the surface of the object and the method further involves: generating a second array of measurement beams; focusing the second array of measurement beams onto the object so that the second array of measurement beams arrives at the surface along a second range of directions characterized by an average angle of incidence that is non-oblique to the surface of the object. Upon interacting with the surface of the object the second array of measurement beams produces a second array of return measurement beams, and the method further involves: combining the second array of return measurement beams from the object with a second array of reference beams to generate a second array of interference beams; and from the second array of interference signals, determining height profile information about the surface of the object. The method further involves using both the height profile information and the oblique angle-of-incidence information to determine locations of features on the surface of the object. Generating and focusing of the first and second arrays of measurement beams takes place concurrently. The method further involves scanning the first and second arrays of measurement beams across the surface of the object.

An advantage of at least some embodiments of the present invention is that the procedures for defect detection and CD determination do not generally require detailed knowledge of the reflecting/scattering properties of different portions of features of the mask.

Another advantage of at least some embodiments of the present invention is that the procedures for defect detection and CD determination generally do no generally require detailed knowledge of the mask composition.

Another advantage of at least some embodiments of the present invention is that the lateral resolution of defect detection and detection of CD errors can be matched to optimum dimensions of sections that are used in an OPC analysis.

Another advantage of at least some embodiments of the present invention is that the measurements for defect detection and CD determination are made with a high throughput.

Another advantage of at least some embodiments of the present invention is that the precision of the CD measurements is sub-nanometer.

Another advantage of at least some embodiments of the present invention is that an optical beam is used instead of a beam of charged particles, e.g., an electron beam such as used in a CD-SEM, to make the measurements for defect detection and CD determination.

Another advantage of at least some embodiments of the present invention is that the measurements for defect detection and CD determination can be made with a large working distance.

Another advantage of at least some embodiments of the present invention is that the measurements for defect detection and CD determination are of the non-contact type.

Another advantage of at least some embodiments of the present invention is that linear displacement interferometric metrology systems are used.

Another advantage of at least some embodiments of the present invention is that differential interferometric microscopy systems are used.

The details of one or more embodiments of the invention are set forth in the accompanying drawings and the description below. Other features, objects, and advantages of the invention will be apparent from the description and drawings, and from the claims.

BRIEF DESCRIPTION OF THE DRAWINGS

FIG. 1k is a schematic diagram of arrays of pinholes, slits, and apertures used in the introduction of reference and measurement beams to an interferometric imaging system and for the selection of the mode of operation of the interferometric imaging system for a particular spot of a measurement object being imaged.

DETAILED DESCRIPTION

Figure 1A:
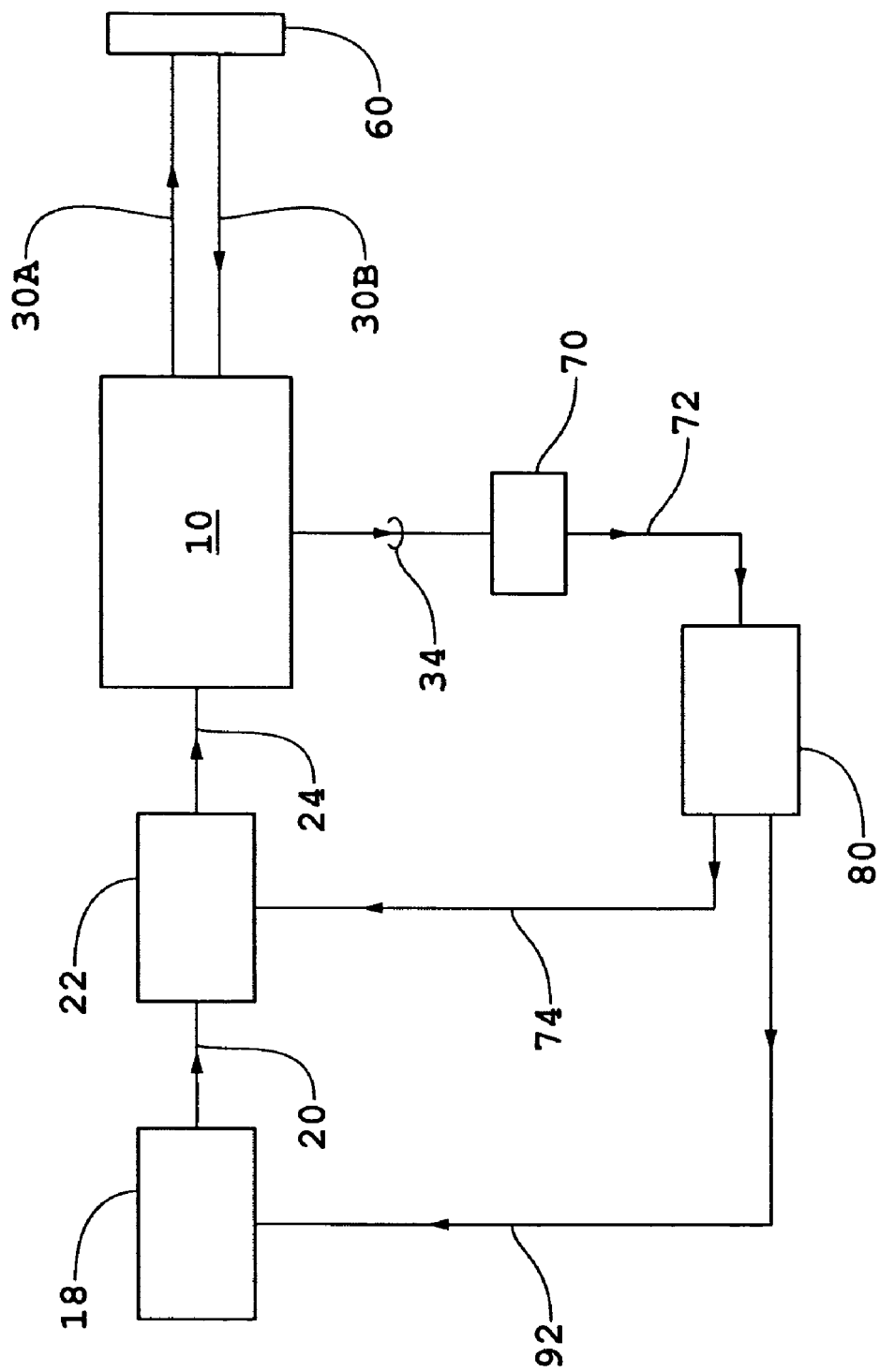
FIG. 1a is a diagram of an interferometric system.

In one group of embodiments of the present invention, a mask is scanned by a linear displacement interferometric metrology system that detects the presence of defects wherein the defects may be in the form of either an error in the physical location of a feature surface and/or an error in the form of a particle. The defects are detected without identifying the source or sources of an error with respect to which of the two forms. After the locations of the defects are detected in the scan of the mask, an interferometric microscopy system, e.g., differential interferometric microscopy system, is used to determine the source of the identified defects at the corresponding locations. The sensitivities of the results of the scan and the subsequent measurements to the different forms of errors are different with respect to each other. As a consequence, the results of the scan and the subsequent measurements can be inverted and the nature with respect to form of each error determined. The differential interferometric microscopy systems may comprise either an interferometric confocal or interferometric non-confocal microscopy system.

In a second group of embodiments of the present invention, there are two complete independent scans of a mask. The first scan of the mask is made using for example a differential interferometric microscopy system for the detection of defects in the forms of a particle and/or defect in the profile of a horizontal surface of the mask or a defect in a CD of a feature of the mask. The first scan is followed by the second scan of the mask for the detection of defects that are in the forms of a particle and/or of errors in one or both of physical locations of two nominally orthogonal boundaries of a feature that lie in a plane transverse and nominally vertical to the nominal surface of the measurement object. The sensitivities of the results of the two scans to the different forms of errors are different with respect to each other. As a consequence, the results of the two scans can be inverted and the nature with respect to form of each error determined.

The electronic processor and controller in the interferometry systems described below is programmed, using techniques that are well known to persons of ordinary skill in the art, to process the interferometric information and perform the data analysis and inversion operations to identify and locate the features/defects on the surface of the object. This processor can be completely local to the interferometry system or it can be a distributed processor with part of it that is local to the interferometry system that it controls and the rest of it located remotely from that system.

The embodiments of the second group of embodiments generally require a longer time for completion of a mask inspection with a concomitant reduction in throughput. However, the second group of embodiments may offer the better overall throughput when the inspection for defects and errors in CD's are used not only in a final mask inspection but incorporated in the manufacturing procedure of the mask as an in process tool.

The measurement of a CD or location of boundary of a feature by either the first or second group of embodiments is based in part on a linear displacement interferometric measurement wherein the measurement and/or the reference object comprises a Porro type prism element such as described in commonly owned U.S. Provisional Patent Applications No. 60/568,774 (ZI-60), No. 60/569,807 (ZI-61), and No. 60/573,196 (ZI-63), all three of which are by Henry A. Hill and are entitled "Apparatus And Methods For Measurement Of Critical Dimensions Of Features And Detection Of Defects In UV, VUV, And EUV Lithography Masks." The contents of each of the three cited applications are herein incorporated in their entirety by reference. The Porro type prism element is formed by two contiguous or adjacent partially reflecting surfaces of an open or filled transparent feature in the mask. The two adjacent contiguous partially reflecting surfaces of the Porro type prism element are nominally orthogonal with respect to each other but may be at some other angle in a given end use application, e.g., 60 degrees or 80 degrees, without departing from the scope and spirit of the present invention.

Figure 4A:
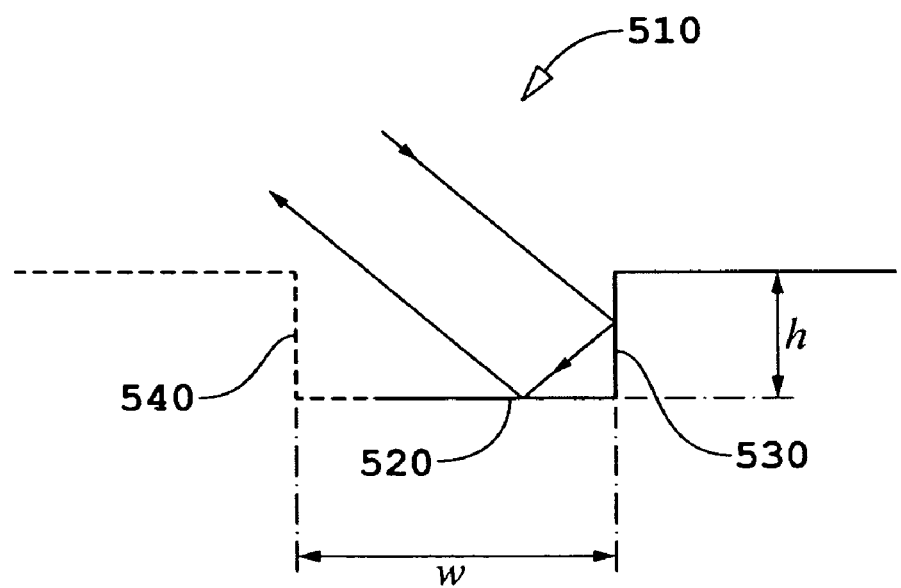
FIG. 4a is a diagrammatic representation of a Porro type prism element formed by surfaces of a mask feature with a beam making two reflections in the Porro type prism element.

An example of the measurement and/or reference object comprising the Porro type prism element is shown diagrammatically as element 510 in FIG. 4*a*. Element 510 comprises two surfaces wherein a partially reflecting horizontal surface 520 forms one of the two reflecting surfaces and a partially reflecting nominally vertical surface of a feature in a mask 530 forms the second of the two reflecting surfaces. The feature comprises surface elements 520, 530, and 540.

A defect in the reflecting substrate 520 in the form of a foreign particle will introduce an error in inferred position of the measurement object in addition to the error introduced by an error in either the profile of surface 520 and/or in a respective CD associated with surfaces 530 and 540. Thus a detected error in the relative locations of respective surfaces of a feature forming a Porro type prism element may be due to either an error in the physical location one or both of the respective feature surfaces and/or due to the presence of a defect, e.g., a particle or an error in the height profile of a surface, within the feature. Accordingly, it is necessary to examine the feature with a different diagnostic tool in order to isolate the contribution of an error in a CD to the linear displacement measurement, i.e., if there is detected an error in the apparent location of a Porro type prism measurement object formed by boundaries of an open or filled transparent feature, a check may be required to eliminate the possibility that a defect exists in the horizontal surface profile or in the form of a particle in the interior of the feature that may be generating the detected error in part or in whole.

The different diagnostic tool comprises a differential interferometric confocal and/or an interferometric non-confocal microscopy system preferentially operating in a dark field mode. The differential interferometric microscopy systems may in addition be used to detect defects in any one of the reflecting surfaces of a mask, i.e., a reflecting substrate, a surface of a buffer, a surface of a phase-shifting layer, and/or a surface of an absorber at different points in the fabrication of the mask.

A CD corresponding to the spacing between two opposing walls of an open or filled transparent feature are measured when using the linear displacement interferometric metrology systems by comparing the respective locations of the respective Porro type prism elements formed by the horizontal and vertical surfaces of the open or filled transparent feature. Thus the measurement of the CD is a differential technique. To the extent that the indices of refraction of the vertical surfaces are the same, the value of the measured CD is independent of the refractive indices of the media forming the surfaces of the open or filled transparent feature.

The pitch of a parallel array of elongated features corresponding to the spacing of corresponding walls of two contiguous open or filled transparent features are measured using the linear displacement interferometric metrology systems by comparing the respective locations of the respective Porro type prism elements formed by the horizontal and vertical surfaces of the open or filled transparent features of the array of elongated features. Thus the measurement of the pitch is a differential technique. To the extent that the indices of refraction of the vertical surfaces are the same and the indices of refraction of the horizontal surfaces are the same, the value of the measured pitch is independent of the refractive indices of the media forming the surfaces of the open or filled transparent features.

The calibration of the pitch scale is based on the use of a reference or standard parallel array and/or on the use of a stage metrology system. The accuracy of a pitch measurement will depend in part on the accuracy to which the surface profile of the array of horizontal reflecting surfaces of the open or filled transparent features are measured or known.

Embodiments of the linear displacement interferometric systems of at least some of the embodiments described herein will first be described with the embodiments of the differential interferometric confocal and non-confocal microscopy systems subsequently described.

Linear Displacement Interferometric Metrology Systems

In at least some of the linear interferometric metrology systems described herein, the generation of measurement beams, the imaging of a substrate, and/or the generation of reference beams may use certain aspects of a confocal microscopy system.

Figure 5:
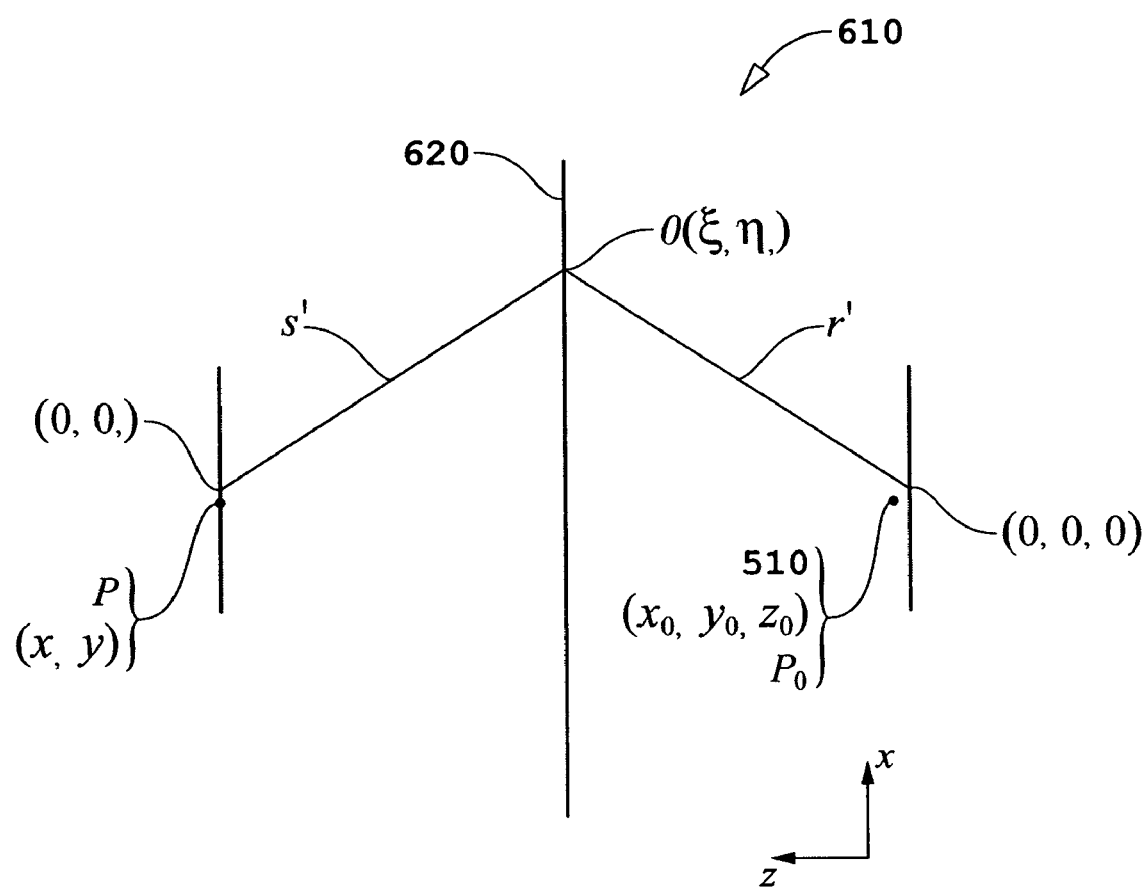
FIG. 5 is a schematic diagram of an imaging system comprising a single lens element.

A general description is first given for the imaging system of the linear displacement interferometric metrology systems used to image of a Porro type prism element of a measurement object. The image comprises fields of measurement beams reflected/scattered by the Porro type prism element. In FIG. 5, the imaging system of the linear displacement interferometric metrology system is represented by an imaging system indicated by element number 610 comprising a single lens element 620. Also shown diagrammatically in FIG. 5 is a Porro type prism element or measurement object 510. The complex amplitude U (P) in the image plane at point P with coordinates (x, y) for a source in the object space at point $P_0$ with coordinates ($x_0$, $y_0$, $z_0$) is given by the equation $$U(P) = Ce^{ik(r'+s')} \int_\eta \int_\xi e^{-ik(p\xi+q\eta)+ik(\xi^2+\eta^2)\frac{z_0}{r'^2}} d\xi d\eta \quad (1)$$

where $\xi$ and $\eta$ are the x and y coordinates of point O in the pupil, $z_0$ is the location of point $P_0$ in the z direction from the plane from which r' is measured, $k=2\pi/\lambda$ is the free space wavenumber for free space wavelength $\lambda$, r' and s' are defined in FIG. 5, and $$p = \frac{x}{s'} + \frac{x_0}{r'}, \quad (2)$$
$$q = \frac{y}{s'} + \frac{y_0}{r'},$$

(see Born and Wolff, *Principles Of Optics*, Pergamon Press). The quantities p and q are also written as $$p = l - l_0, \quad (3)$$
$$q = m - m_0,$$
where
$$l_0 = -\frac{x_0}{r'}, \, l = \frac{x}{s'}, \quad (4)$$
$$m_0 = -\frac{y_0}{r'}, \, m = \frac{y}{s'}.$$

The open and filled transparent features of a mask generally comprise high aspect ratios with respect to feature lengths and widths. This property is used to advantage by specifying the pupil of the imaging system to be rectangular in cross-section with the boundaries of the rectangle aligned with the boundaries of the features and selecting the aspect ratio of the rectangle to optimize performance of the linear displacement interferometric metrology system. The use of a pupil that is rectangular in cross-section makes it possible to decouple the properties of the measured conjugated quadratures of the fields reflected/scattered by the feature with respect to the $\xi$ and $\eta$ coordinates. As a consequence, it is simpler to optimize a design of an imaging system in the linear displacement interferometric metrology system and makes it possible to achieve a better performance with respect to signal-to-noise ratios.

The component of a measurement beam that is generated by reflecting/scattering a measurement beam by the open or filled transparent feature will generally comprise two components, a backscattered component and a forward scattered component. The primary contribution to the backscattered component will be generated by an even number of multiple reflections in Porro type prism elements formed by the bottom of a feature and a contiguous or associated wall of the feature. The primary contribution to the forward reflected/scattered component will be generated by a single reflection at a horizontal surface of the feature and/or of the horizontal surface of the surrounding substrate, by an odd number of multiple reflections in Porro type prism elements formed by the bottom of a feature and contiguous or associated walls of the feature, and by scattering by the aperture formed by the top of the feature.

In at least some embodiments, the conjugated quadratures of the backscattered component are measured interferometrically and accordingly, the phase of the conjugated quadratures contains information about the location of the Porro type prism element in one or more of the x, y, and z directions. Two procedures may be used to measure the backscattered component generated by a double reflection in a Porro type prism element formed by two contiguous or associated surfaces of the open or filled transparent feature.

One procedure is to restrict the range of values in $\xi$ in Equation (1) to eliminate both the forward reflected/scattered component and to prevent the generation of contributions to the reflected/scattered component by even numbers of multiple reflections of 4 or greater in the measured conjugated quadratures.

Another procedure is to restrict the range of values in $\xi$ in Equation (1) to prevent the generation of contributions to the backscattered component by an even numbers of multiple reflections of 4 or greater in the measured conjugated quadratures but not to eliminate the contribution of forward reflected/scattered component in the measured conjugated quadratures. The contributions of the forwarded/scattered components and the backscattered component are separated in the another procedure by the use of a form of phase sensitive detection such as described in commonly owned U.S. Provisional Patent Application No. 60/460,129 (ZI-51) and in U.S. patent application Ser. No. 10/816,172 (ZI-51) wherein both are entitled "Apparatus and Method for Measurement of Fields of Forward Scattered/Reflected and Backscattered Beams by an Object in Interferometry" and both of which are by Henry A. Hill. The contents of the provisional and non-provisional patent applications are herein incorporated in their entirety by reference. The contributions of the forwarded/scattered components and the backscattered component are separated in a subsequently described variant of the second embodiment of the present invention.

Figure 4B:
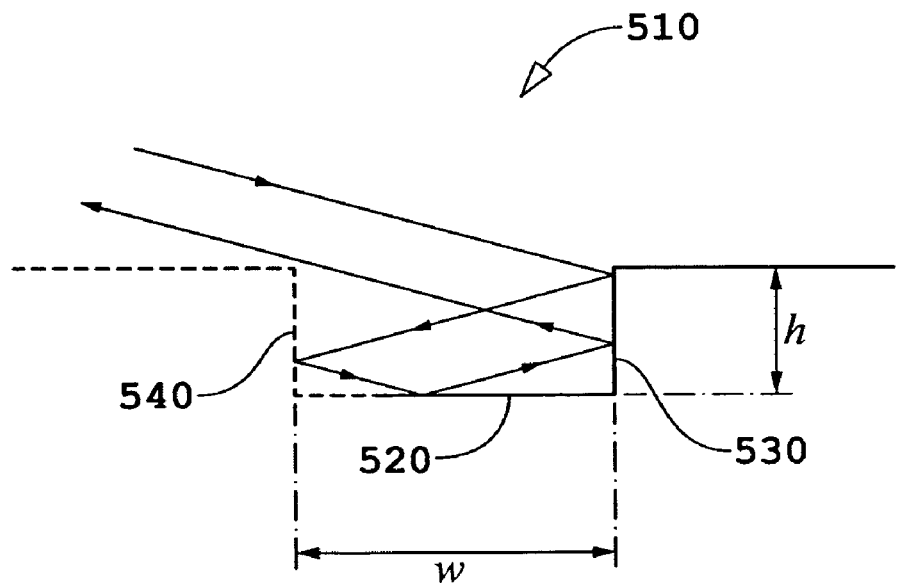
FIG. 4b is a diagrammatic representation of an open feature in a mask comprising a Porro type prism element with a beam making four reflections at the surfaces of the open feature.

The subsequent general description of the properties in the image plane of a linear displacement interferometric metrology system will be restricted to the first procedure wherein the range of values in $\xi$ is restricted, i.e., $\xi_2 > \xi_1$ and $\xi_1 \geq 0$ and $\xi_2$ selected to prevent the generation of contributions to the reflected/scattered component by even numbers of multiple reflections of 4 or greater in the measured conjugated quadratures. The value of $\xi_2$ will be determined by the height of the wall of the feature relative to the respective width of the feature and consideration of the amplitude of a component generated by four reflections at surfaces of the feature (see FIG. 4b). For a height h and a width w (see FIG. 4b), the corresponding value limiting value $\xi_{2,lim}$ is given by the relationship $$\left(\frac{\xi_{2,lim}}{s'}\right) = \left(\frac{3}{2}\right)\left(\frac{w}{h}\right). \quad (5)$$

For the example of h=100 nm and w=200 nm, the corresponding limiting value $\xi_{2,lim}$ is $$\xi_{2,lim} = 3s' \quad (6)$$
with
$$\arctan\left(\frac{\xi_{2,lim}}{s'}\right) = 71.6 \text{ degrees.}$$

It is important to note that the relative large value for $\arctan(\xi_{2,lim}/s')$ makes it possible to achieve a significant spatial resolution in the $\xi$ direction at the feature being imaged.

Equation (1) is evaluated for U (P) based on a rectangular aperture at the pupil and using a power series representation for the respective integrand. The leading terms from that evaluation are $$U(P) = 4a_\xi a_\eta C e^{ik(r'+s')-ik\left[(p\xi_0+q\eta_0)-\frac{1}{2}(\xi_0^2+\eta_0^2)\frac{z_0}{r'^2}\right]} \times \quad (7)$$

$$\left\{\begin{array}{l} \operatorname{sinc} k\alpha_\xi a_\xi \operatorname{sinc} k\alpha_\eta a_\eta - k\left(\frac{\beta a_\xi^2}{2}\right)^2 f_2(k\alpha_\xi a_\xi) - \\ \qquad k\left(\frac{\beta a_\eta^2}{2}\right)^2 f_2(k\alpha_\eta a_\eta) - \\ \qquad 2k\left(\frac{\beta a_\xi^2}{2}\right)\left(\frac{\beta a_\eta^2}{2}\right) f_1(k\alpha_\xi a_\xi) f_1(k\alpha_\eta a_\eta) + \ldots + \\ \qquad i\left[k\left(\frac{\beta a_\xi^2}{2}\right) f_1(k\alpha_\xi a_\xi) + k\left(\frac{\beta a_\eta^2}{2}\right) f_1(k\alpha_\eta a_\eta)\right] + \ldots \end{array}\right.$$

where $$\beta = \frac{z_0}{r'^2}, \quad (8)$$
$$\xi_0 = \frac{(\xi_2+\xi_1)}{2}, \eta_0 = \frac{(\eta_2+\eta_1)}{2},$$
$$\alpha_\xi = p - \xi_0\beta, \alpha_\eta = q - \eta_0\beta,$$
$$a_\xi = \frac{(\xi_2-\xi_1)}{2}, a_\eta = \frac{(\eta_2-\eta_1)}{2}.$$

and $$f_1(k\alpha a) = \operatorname{sinc} k\alpha a - 2\left[\frac{\cos k\alpha a - \operatorname{sinc} k\alpha a}{(k\alpha a)^2}\right] \quad (9)$$
$$= \frac{1}{3} - \frac{(k\alpha a)^2}{5} + \ldots,$$
$$f_2(k\alpha a) = \operatorname{sinc} k\alpha a + 4[\cos k\alpha a - 3f_1(k\alpha a)] \quad (10)$$
$$= \frac{1}{5} + \ldots.$$

The properties of the measurement and reference beams are described in the context of specific embodiments of the present invention. However, it is appropriate to describe here a general property of various embodiments which is achieved through the design of the reference beams used in the linear displacement interferometric metrology systems. The general property is that the reference beam is generated with properties such that the phase Φ of conjugated quadratures corresponding to the interference cross-term in the electrical interference signal values between the reference beam and the reflected/scattered measurement beam from a given Porro type prism element generated by detection of mixed output beams of the linear displacement interferometric metrology systems has no dependence on either x or y.

The point spread function represented by Equation (7) for the imaging system can be used to derive the dependence of the phase Φ on the location of a spot being imaged by the interferometric imaging system. For apertures 62 of pinhole array 12 that are less than or of the order of the size of the resolution of the imaging system 100, phase Φ is within a constant offset value determined to a good approximation as the phase of U (P) given by Equation (7) minus the corresponding phase of the reference beam. The result is expressed as $$\Phi = 2k\left(\frac{x\xi_0+y\eta_0}{s'}\right) - 2k(x\sin\vartheta_\xi + y\sin\vartheta_\eta) + \quad (11)$$

-continued
$$2k\left(\frac{x_0\xi_0+y_0\eta_0}{r'}\right) +$$
$$k(\xi_0^2+\eta_0^2)\frac{z_0}{r'^2} +$$
$$2\arctan\left\{\frac{kz_0}{6\operatorname{sinc} k\alpha_\xi a_\xi \operatorname{sinc} k\alpha_\eta a_\eta}\frac{(a_\xi^2+a_\eta^2)}{r'^2}\right\} + \ldots$$

where the term (x sin θ$_\xi$+y sin θ$_\eta$) corresponds to the phase contribution of the reference beam and θ$_\xi$ and θ$_\eta$ are the angles of incidence of the reference beam at the image plane, respectively. It is evident on inspection of Equation (11) that the x and y dependence of phase Φ will be eliminated when the phase term (x sin θ$_\xi$+y sin θ$_\eta$) for the reference beam is designed such that $$\sin\nu_\xi = \frac{\xi_0}{s'}, \quad (12)$$

$$\sin\nu_\eta = \frac{\eta_0}{s'}. \quad (13)$$

Equations (12) and (13) represent a condition that is met in certain embodiments and accordingly, the general property is a property of those embodiments.

This is an important feature since the phase represented in conjugated quadratures is a function only of the reflecting properties and location of the Porro type prism element in addition to a fixed offset error in the linear displacement interferometric metrology systems. A corollary statement is that the accuracy to which the location of a surface of an open or filled transparent feature can be measured is not affected by displacements of a pinhole corresponding to a detector or of a detector pixel used in measuring the respective conjugated quadratures.

In the following description of the different embodiments, many elements of the different embodiments perform like functions and are indicated with the same numerals in different respective figures of the embodiments.

Referring to FIG. 1a, an interferometric metrology system is shown diagrammatically comprising an interferometer 10, a source 18, a beam-conditioner 22, detector 70, an electronic processor and controller 80, and a measurement object 60. Source 18 is a pulsed or shuttered source that generates input beam 20 comprising one or more frequency components. Beam 20 is incident on and exits beam-conditioner 22 as input beam 24 that comprises a single polarized component or two orthogonally polarized components. Each of the polarized components comprises one or more different frequency components. The measurement beam components of the frequency components of input beam 24 are coextensive in space and may have the same or different temporal window functions and the corresponding reference beam components are coextensive in space and may have the same or different temporal window functions.

Reference and measurement beams may be generated in either beam-conditioner 22 from a set of beams from source 18 or in interferometer 10 for each of the frequency components of input beam 24. Measurement beam 30A generated in either beam-conditioner 22 or in interferometer 10 is incident on measurement object 60. Measurement beam 30B is a return measurement beam generated as either a portion of measurement beam 30A reflected and/or scattered or transmitted by measurement object 60. Return measurement beam 30B is combined with the reference beam in interferometer 10 to form output beam 34.

Output beam 34 is detected by a quantum detection process by detector 70 to generate one or more electrical interference signals per source pulse for the homodyne detection method used and transmitted as signal 72. Detector 70 may comprise an analyzer to select common polarization states of the reference and return measurement beam components of beam 34 to form a mixed beam. Alternatively, interferometer 10 may comprise an analyzer to select common polarization states of the reference and return measurement beam components such that beam 34 is a mixed beam.

In practice, known phase shifts are introduced between the reference and measurement beam components of output beam 34 by two different techniques. In the first technique, phase shifts are introduced between corresponding reference and measurement beam components for each of the frequency components of output beam 34 as a consequence of a non-zero optical path difference between the reference and measurement beam paths in interferometer 10 and corresponding frequency shifts introduced to the frequency components of input beam 24 by beam-conditioner 22 and/or source 18 as controlled by signals 74 and 92, respectively, from electronic processor and controller 80. In the second technique, phase shifts are introduced between the reference and measurement beam components for each of the frequency components of input beam 24 by beam-conditioner 22 and/or source 18 as controlled by signals 74 and 92, respectively, from electronic processor and controller 80.

There are different ways to configure source 18 and beam-conditioner 22 to meet the input beam requirements of the different embodiments of the present invention. Examples of beam-conditioners that may be used in either first or the second technique comprise combinations of a two frequency generator and phase shifting type of beam-conditioner such as described in commonly owned U.S. patent application Ser. No. 10/765,368 (ZI-47) entitled "Apparatus and Method for Joint Measurements of Conjugated Quadratures of Fields of Reflected/Scattered and Transmitted Beams by an Object in Interferometry". Other examples of beam-conditioners that may be used in either the first or the second technique comprise combinations of multiple frequency generators and phase shifting types of beam-conditioners such as described for example in commonly owned U.S. patent application Ser. No. 10/816,180 (ZI-50) also entitled "Apparatus and Method for Joint Measurement of Fields of Scattered/Reflected Orthogonally Polarized Beams by an Object in Interferometry". The two U.S. Patent Applications are by Henry A. Hill and the contents thereof are incorporated herein in their entirety by reference.

With a continuation of the description of different ways to configure source 18 and beam-conditioner 22 to meet the input beam requirements of different embodiments of the present invention, source 18 will preferably comprise a pulsed source. There are a number of different ways for producing a pulsed source [see Chapter 11 entitled "Lasers", *Handbook of Optics*, 1, 1995 (McGraw-Hill, New York) by W. Silfvast]. Each pulse of source 18 may comprise a single pulse or a train of pulses such as generated by a mode locked Q-switched Nd:YAG laser. A single pulse train is referenced herein as a pulse and a pulse and a pulse train are used herein interchangeably.

Source 18 may be configured in certain embodiments of the present invention to generate two or more frequencies by techniques such as described in a review article entitled "Tunable, Coherent Sources For High-Resolution VUV and XUV Spectroscopy" by B. P. Stoicheff, J. R. Banic, P. Herman, W. Jamroz, P. E. LaRocque, and R. H. Lipson in *Laser Techniques for Extreme Ultraviolet Spectroscopy*, T. J. McIlrath and R. R. Freeman, Eds., (American Institute of Physics) pp 19 (1982) and references therein. The techniques include for example second and third harmonic generation and parametric generation such as described in the articles entitled "Generation of Ultraviolet and Vacuum Ultraviolet Radiation" by S. E. Harris, J. F. Young, A. H. Kung, D. M. Bloom, and G. C. Bjorklund in *Laser Spectroscopy I*, R. G. Brewer and A. Mooradi, Eds. (Plenum Press, New York) pp 59, (1974) and "Generation of Tunable Picosecond VUV Radiation" by A. H. Kung, *Appl. Phys. Lett.* 25, pp 653 (1974). The contents of the three cited articles are herein incorporated in their entirety by reference.

The output beams from source 18 comprising two or more frequency components may be combined in beam-conditioner 22 by beam-splitters to form coextensive measurement and reference beams that are either spatially separated or coextensive as required in certain embodiments. The frequency shifting of the various components required in certain embodiments may be introduced in source 18 for example by frequency modulation of input beams to parametric generators and the phase shifting of reference beams relative to measurement beams in beam-conditioner 22 may be achieved by phase shifters of the optical-mechanical type comprising for example prisms or mirrors and piezoelectric translators or of the electro-optical modulator type.

Figure 1B:
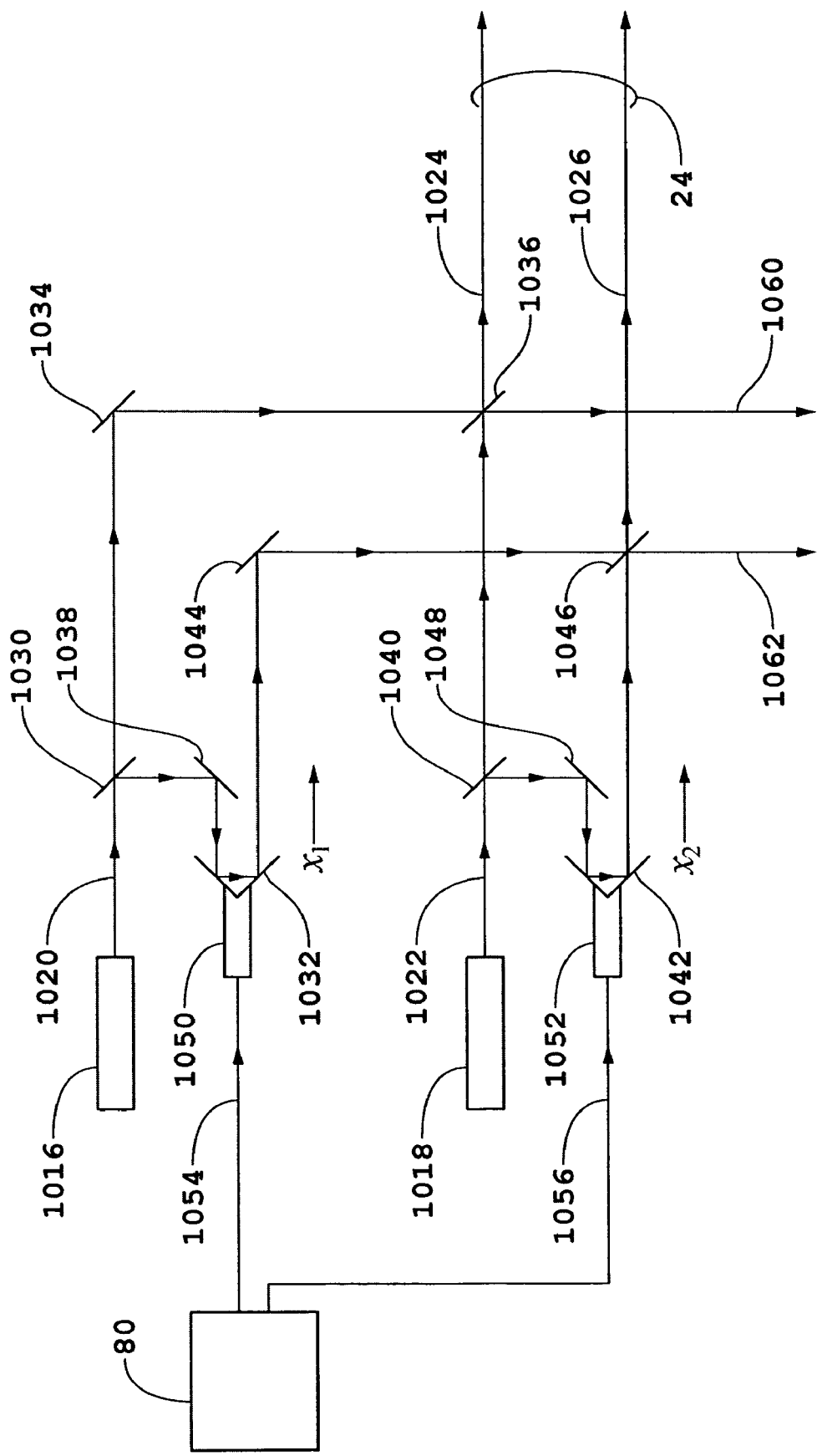
FIG. 1b is a diagram of a source and beam-conditioner.

An embodiment of the optical-mechanical type of beam-conditioner and two frequency generator that may be used in the phase shifting of reference beams relative to measurement beams in beam-conditioner 22 is shown diagrammatically in FIG. 1*b*. The source comprises two lasers 1016 and 1018 operating at two closely spaced but different frequencies; non-polarizing beam-splitters 1030, 1036, 1040, and 1046; retroreflectors 1032 and 1042; and mirrors 1034, 1038, 1044, and 1048. The positions of retroreflectors 1032 and 1042 are controlled by transducers 1050 and 1052, respectively, according to signals 1054 and 1056, respectively, from electronic processor and controller 80. Beams 1020 and 1022 generated by lasers 1016 and 1018, respectively, are incident on non-polarizing beam-splitters 1030 and 1040, respectively. Beams 1020 and 1022 are plane polarized in a plane oriented at 45° with respect to the plane of FIG. 1*b*.

A first portion of beam 1020 is transmitted by beam-splitter 1030 and reflected by mirror 1034 and beam-splitter 1036 as a first component of a reference beam 1024 and a second portion of beam 1020 is reflected by beam-splitter 1030, mirror 1038, retroreflector 1032, mirror 1044, and beam-splitter 1046 as a first component of a measurement beam 1026. A first portion of beam 1022 is transmitted by beam-splitter 1040 and beam-splitter 1036 as a second component of reference beam 1024 and a second portion of beam 1022 is reflected by beam-splitter 1040, mirror 1048, retroreflector 1042, and transmitted by beam-splitter 1046 as a second component of measurement beam 1026.

A second set of measurement and reference beams are also generated as beams 1062 and 1060, respectively, that can be used as measurement and reference input beams for an interferometer system different from the interferometer system for which beams 1026 and 1024 are input measurement and reference beams, respectively. A third portion of beam 1020 is transmitted by beam-splitter 1030, reflected by mirror 1034, and transmitted by beam-splitter 1036 as a first component of a reference beam 1060 and a fourth portion of beam 1020 is reflected by beam-splitter 1030, mirror 1038, retroreflector 1032, and mirror 1044, and transmitted by beam-splitter 1046 as a first component of a measurement beam 1062. A third portion of beam 1022 is transmitted by beam-splitter 1040 and reflected by beam-splitter 1036 as a second component of reference beam 1060 and a fourth portion of beam 1022 is reflected by beam-splitter 1040, mirror 1048, retroreflector 1042, and beam-splitter 1046 as a second component of measurement beam 1062.

Displacements $x_1$ and $x_2$ of retroreflectors 1032 and 1042, respectively, by transducers 1050 and 1052, respectively, will introduced relative a phase shift $\Delta\phi_1$ between the first measurement and first reference beam components of beams 1026 and 1024 and a relative phase shift $\Delta\phi_2$ between the second measurement and second reference beam components of beams 1026 and 1024. The relationship between displacements $x_1$ and $x_2$ and the phase shifts $\Delta\phi_1$ and $\Delta\phi_2$ are given by the following formulae:

$$\Delta\phi_1 = -2kx_1,$$

$$\Delta\phi_2 = -2kx_2. \qquad (14)$$

Reference and measurement beams 1024 and 1026 each with coextensive components may be used as spatially separated components of input beam 24 or combined by a non-polarizing beam-splitter (not shown in a figure) to form input beam 24 with spatially coextensive components for various embodiments.

The general description is continued with reference to FIG. 1a. Input beam 24 is incident on interferometer 10 wherein reference beams and measurement beams are generated. The reference beams and measurement beams comprise one or two arrays of reference beams and one or two arrays of measurement beams, respectively, for measurements using measurement beams that comprise a single polarization state or two orthogonal polarization states, respectively, wherein the arrays may comprise arrays of one element. The arrays of measurement beams are focused on and/or in measurement object 60 and arrays of return measurement beams are generated by reflection/scattering by measurement object 60. The arrays of reference beams and return measurement beams are combined by a beam-splitter to form one or two arrays of output beams using measurement beams that comprise a single polarization state or two orthogonal polarization states, respectively. The arrays of output beams are mixed with respect to state of polarization either in interferometer 10 or in detector 70. The arrays of output beams are subsequently focused to spots on pixels of a multipixel detector and detected by a quantum detection process to generate the array of electrical interference signals 72.

The conjugated quadratures of fields of return measurement beams are obtained by using a single-, double-, bi-, quad-homodyne detection method or variant thereof. The bi- and quad-homodyne detection methods are described for example in cited U.S. patent application Ser. No. 10/765,368 (ZI-47). The variants of the bi- and quad-homodyne detection methods are described for example in cited U.S. patent application Ser. No. 10/816,180 (ZI-50).

For the single-homodyne detection method, input beam 24 comprises a single frequency component and sets of four or eight measurements of the array of electrical interference signals 72 is made in non-ellipsometric or ellipsometric measurements, respectively. For each of the measurements of the array of electrical interference signals 72 in non-ellipsometric and ellipsometric measurements, known phase shifts are introduced between each reference beam component and respective return measurement beam component of output beam 34. The subsequent data processing procedure used to extract the conjugated quadratures of fields of beams reflected and/or scattered by a substrate is described for example in cited U.S. Pat. No. 6,445,453 (ZI-14).

The double-homodyne detection method which is applicable to non-ellipsometric measurements uses input beam 24 comprising four frequency components and four detectors to obtain measurements of electrical interference signals that are subsequently used to obtain conjugated quadratures in non-ellipsometric measurements. Each detector element of the four detector elements obtains a different one of the four electrical interference signal values with the four electrical interference signal values obtained simultaneously to compute the conjugated quadratures for a field. Each of the four electrical interference signal values contains only information relevant to one orthogonal component of the conjugated quadratures. The double-homodyne detection used herein is related to the detection methods such as described in Section IV of the article by G. M D'ariano and M G. A. Paris entitled "Lower Bounds On Phase Sensitivity In Ideal And Feasible Measurements," *Phys. Rev. A* 49, 3022-3036 (1994). Accordingly, the double-homodyne detection method does not make joint determinations of conjugated quadratures of fields wherein each electrical interference signal value contains information simultaneously about each of two orthogonal components of the conjugated quadratures.

In the adaptation of the double-homodyne detection method to ellipsometric measurements, input beam 24 comprises eight frequency components and eight detectors to obtain measurements of eight electrical interference signals that are subsequently used to obtain conjugated quadratures. Each detector element of the eight detector elements obtains a different one of the eight electrical interference signal values with the eight electrical interference signal values obtained simultaneously to compute the conjugated quadratures of fields of scattered/reflected orthogonally polarized fields. Each of the eight electrical interference signal values contains only information relevant to one orthogonal component of one of the two conjugated quadratures.

The bi- and quad-homodyne detection methods obtain measurements of electrical interference signals wherein each measured value of an electrical interference signal contains simultaneously information about two orthogonal components of conjugated quadratures. The two orthogonal components correspond to orthogonal components of conjugated quadratures such as described in cited U.S. patent application Ser. No. 10/765,368 (ZI-47).

The variants of the bi- and quad-homodyne detection methods obtain measurements of electrical interference signals wherein each measured value of an electrical interference signal contains simultaneously information about two orthogonal components of each of two conjugated quadratures of fields of scattered/reflected orthogonally polarized beams. The two orthogonal components of the two conjugated quadratures correspond to orthogonal components of conjugated quadratures such as described in cited U.S. patent application Ser. No. 10/816,180 (ZI-50).

Figure 1C:
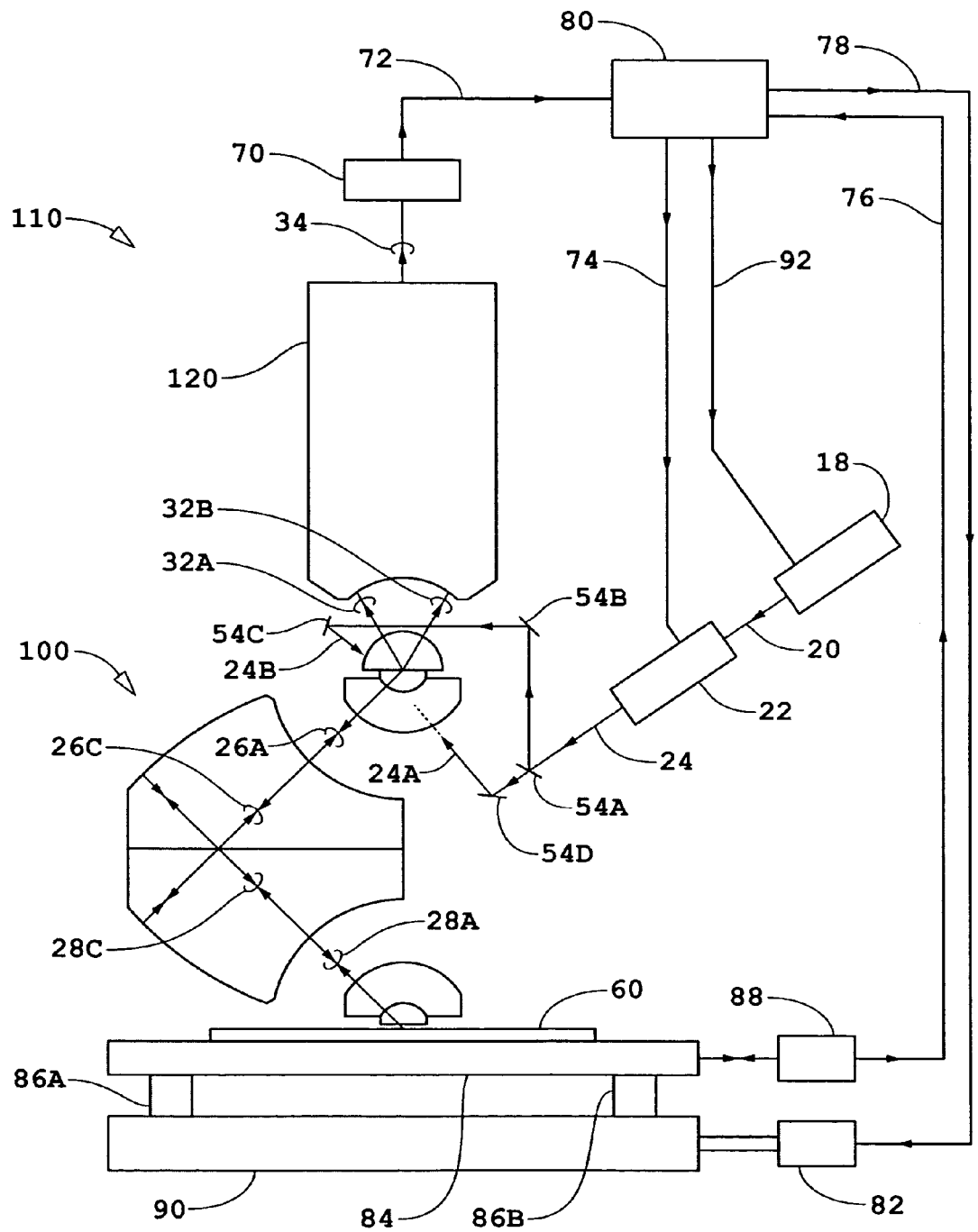
FIG. 1c is a diagram of an interferometric metrology system comprising a catadioptric imaging system.

A first embodiment is shown schematically in FIG. 1c. The first embodiment measures the lateral positions of features and/or defects of a measurement object and comprises a first imaging system generally indicated as numeral 100, pinhole array beam-splitter 12, detector 70, and a second imaging system generally indicated as numeral 110. The second imaging system 110 is low power microscope having a large working distance, e.g. Nikon ELWD and SLWD objectives and Olympus LWD, ULWD, and ELWD objectives.

Figure 1D:
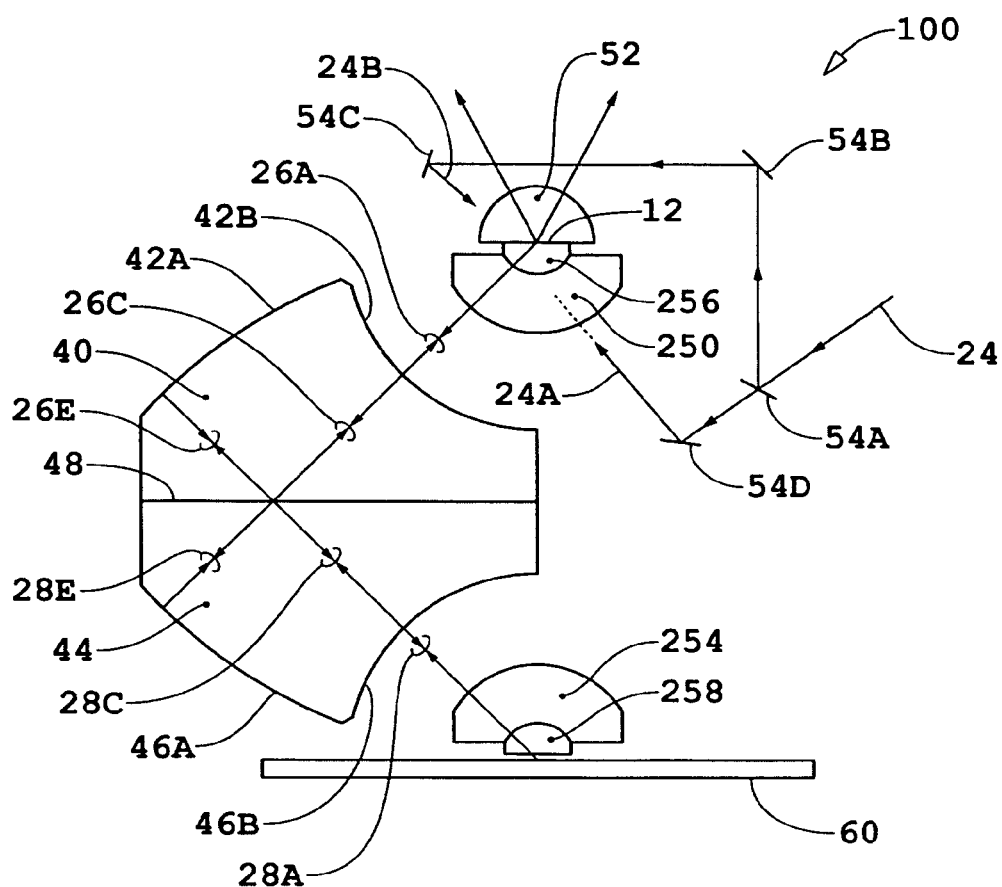
FIG. 1d is a diagram of a catadioptric imaging system.

The first imaging system 100 is shown schematically in FIG. 1*d*. Imaging system of interferometer 100 is a catadioptric system such as described in commonly owned U.S. Pat. No. 6,552,852 B2 (ZI-38) and U.S. Pat. No. 6,717,736 (ZI-43) wherein both are entitled "Catoptric and Catadioptric Imaging System" and both are to Henry A. Hill. The contents of the two cited patents are incorporated herein in their entirety by reference.

The description of interferometer 100, a source 18, beam-conditioner 22, detector 70, and electronic processor and controller 80 is the same as corresponding portions of the descriptions of catoptric and catadioptric imaging systems given in U.S. patent application Ser. No. 10/866,010 (ZI-52), entitled "Apparatus and Method for High Speed Scan for Subwavelength Defects in Semiconductor Metrology," by Henry A. Hill, the contents of which is incorporated herein by reference. A number of different catadioptric imaging systems for far-field and near-field interferometric confocal microscopy have been described, for example, see U.S. Pat. Nos. 6,552,852 (ZI-38) and 6,717,736 (ZI-43); U.S. Provisional Patent Application Nos. 60/485,255, entitled "Apparatus and Method for Ellipsometric Measurements with High Spatial Resolution," (ZI-53); 60/501,666, entitled "Catoptric and Catadioptric Imaging Systems With Adaptive Catoptric Surfaces," (ZI-54); and 60/506,715, entitled "Catoptric and Catadioptric Imaging Systems Comprising Pellicle Beam-Splitters And Non-Adaptive And Adaptive Catoptric Surfaces," (ZI-56); and U.S. patent applications No. 10/778,371, entitled "Transverse Differential Interferometric Confocal Microscopy," (ZI-40); Ser. No. 10/782,057, entitled "Longitudinal Differential Interferometric Confocal Microscopy," (ZI-41); Ser. No. 10/782,058, entitled "Method And Apparatus For Dark Field Interferometric Confocal Microscopy," (ZI-42); Ser. No. 10/765,229, entitled "Interferometric Confocal Microscopy Incorporating Pinhole Array Beam-Splitter," (ZI-45); Ser. No. 10/816,180, entitled "Apparatus and Method for Joint Measurement Of Fields Of Orthogonally Polarized Beams Scattered/Reflected By An Object In Interferometry," (ZI-50); Ser. No. 10/886,157, filed Jul. 7, 2004, entitled "Apparatus And Method For Ellipsometric Measurements With High Spatial Resolution," (ZI-53); Ser. No. 10/938,408, filed Sep. 10, 2004, entitled "Catoptric And Catadioptric Imaging Systems With Adaptive Catoptric Surfaces," (ZI-54); and Ser. No. 10/948,959, filed Sep. 24, 2004, entitled "Catoptric And Catadioptric Imaging Systems With Pellicle And Aperture-Array Beam-Splitters And Non-Adaptive And Adaptive Catoptric Surfaces," (ZI-56), all of which are by Henry A. Hill and are incorporated herein in their entirety by reference. Other forms of non-catoptric or non-catadioptric microscopy imaging systems may be used for interferometer 100 without departing from the spirit or scope of the present invention.

Figure 1E:
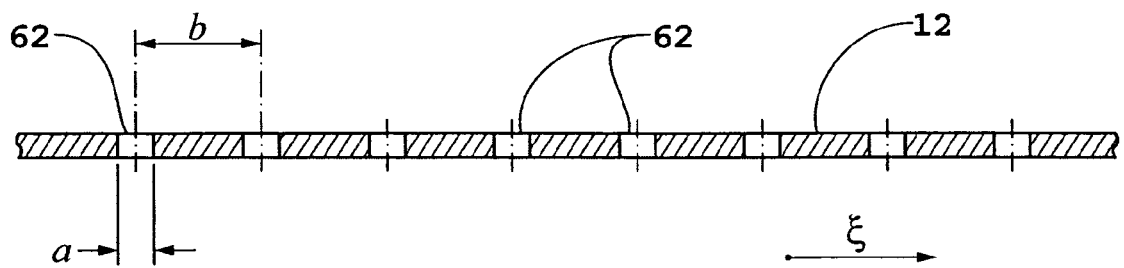
FIG. 1e is a diagram of a pinhole array beam-splitter.
Figure 1F:
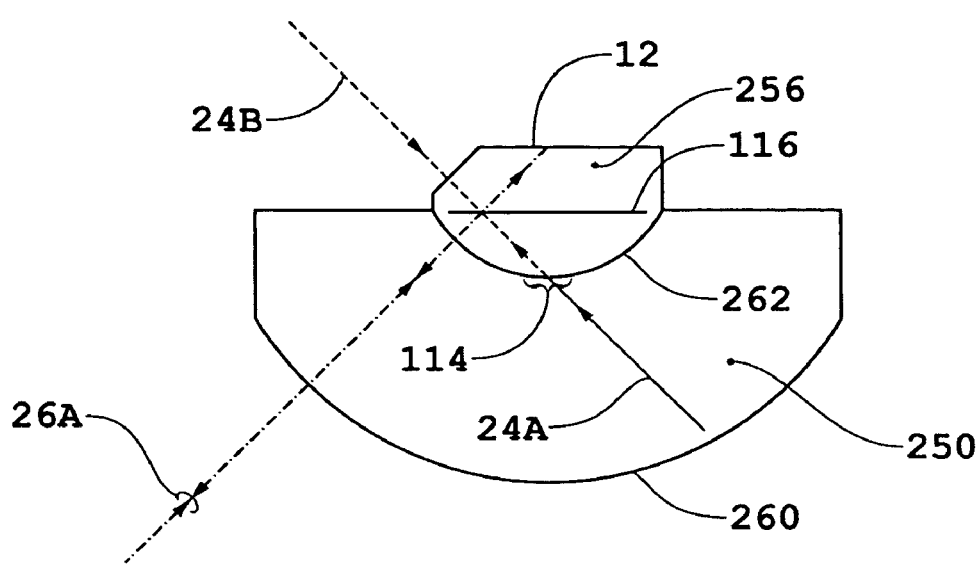
FIG. 1f is a diagram of a beam-splitter system for introducing measurement and reference beams into an interferometric metrology system.
Figure 1G:
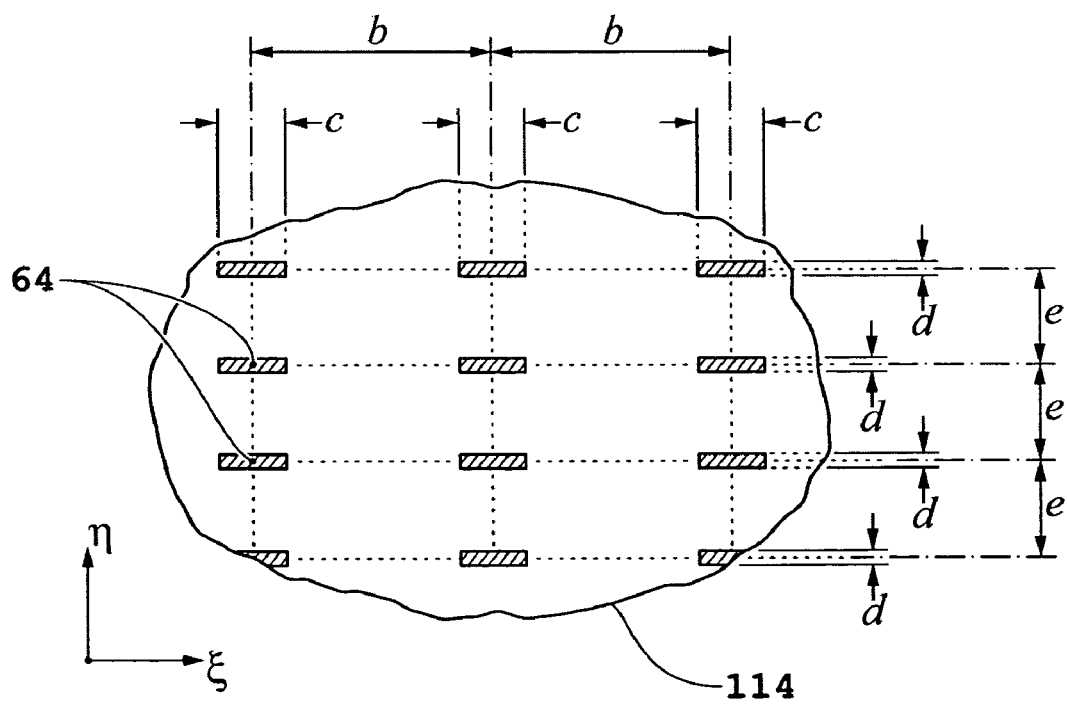
FIG. 1g is a diagram of a slit array.

With reference to FIG. 1*c*, the reference and measurement beam components of input beam 24 exit beam conditioner 22 as spatially separated beams. The spatially separated measurement beam component of input beam 24 is not incident on mirror 54A, although shown in FIG. 1*c* as being transmitted, and reflected by mirror 54D as measurement beam 24A. The reference beam component of beam 24 is reflected by mirror 54A as reference beam 24B after reflection by mirrors 54B and 54C. Measurement beam 24A is incident on slits 64 of a slit-array 114 and a portion thereof transmitted as an array of diffracted measurement beams as shown in FIG. 1*f*. The slits of slit-array 114 are conjugates of pinholes 62 of pinhole array 12 with respect to beam-splitter 116. A schematic diagram of slit-array 114 is shown in FIG. 1*g* where the length and width of the slits are c and d, respectively. The spacings of slits 64 in the $\xi$ and $\eta$ directions of the pupil are b and e, respectively. Spacings b and e may be the same or different as shown in FIG. 1*g*.

The array of diffracted measurement beams is incident on non-polarizing beam-splitter 116 and a portion thereof reflected as an array of measurement beams forming the measurement beam component of beam 26A. Reference beam 24B is incident on non-polarizing beam-splitter 116 and a portion thereof reflected as the reference beam component of the beam incident on pinhole array beam-splitter 12 (see FIG. 1*e*). The optical elements in FIG. 1*f* correspond to the optical elements in FIG. 1*d*.

The angle of incidence of the reference beam component incident on pinhole array beam-splitter 12 is selected to meet the condition specified with respect to the general property described following Equation (10) herein. The very general property has to do with the absence of a x dependence in the interference cross-term between the reference beam and the reflected/scattered measurement beam from a given Porro type prism element in the electrical interference signal values.

The direction of the slits in slit-array 114 is parallel to the plane of FIGS. 1*c* and 1*d* and parallel to the $\xi$ direction (see FIGS. 1*g* and 5 and related discussion). The length and width of the slits c and d, respectively, are selected such that the effect of diffraction on the transmitted portion of measurement beam 24A is to generate for each beam of the array of diffracted measurement beams a beam divergence in the $\xi$ and $\eta$ directions, respectively that cover the desired ranges in $\xi$ and $\eta$, i.e., $\xi_1 \leq \xi \leq \xi_2$ and $\eta_1 \leq \eta \leq \eta_2$ (see discussion related to FIG. 5). Since the location of slits of slit-array 114 are at conjugate positions of pinholes of pinhole array 112 with respect to beam-splitter 116, the slits of slit-array 114 and conjugate pinholes of pinhole array 12 are imaged by imaging system 100 to the same conjugate spots in the space of measurement object 60.

Figure 2A:
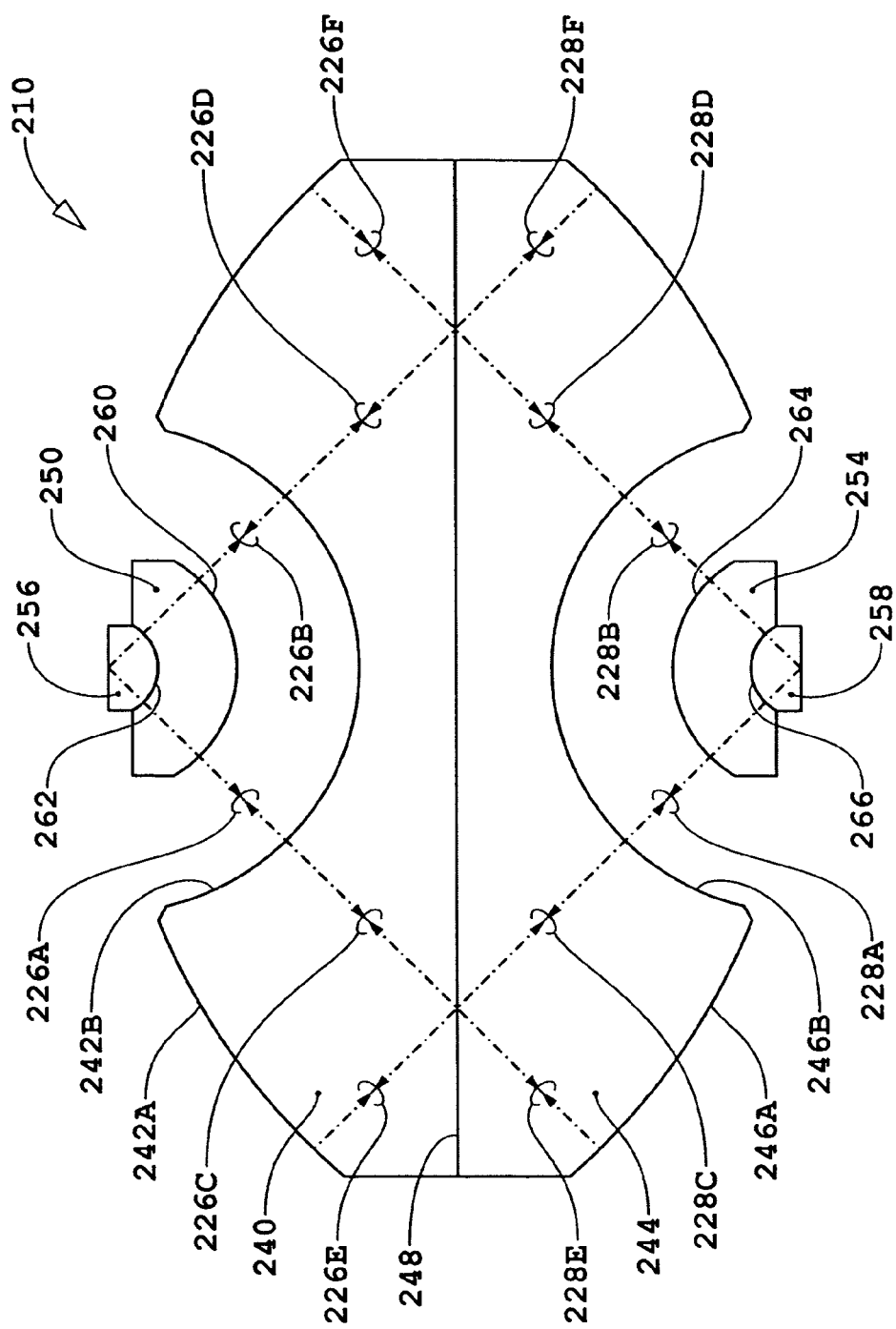
FIG. 2a is a schematic diagram of an achromatic astigmatic catadioptric imaging system.
Figure 2B:
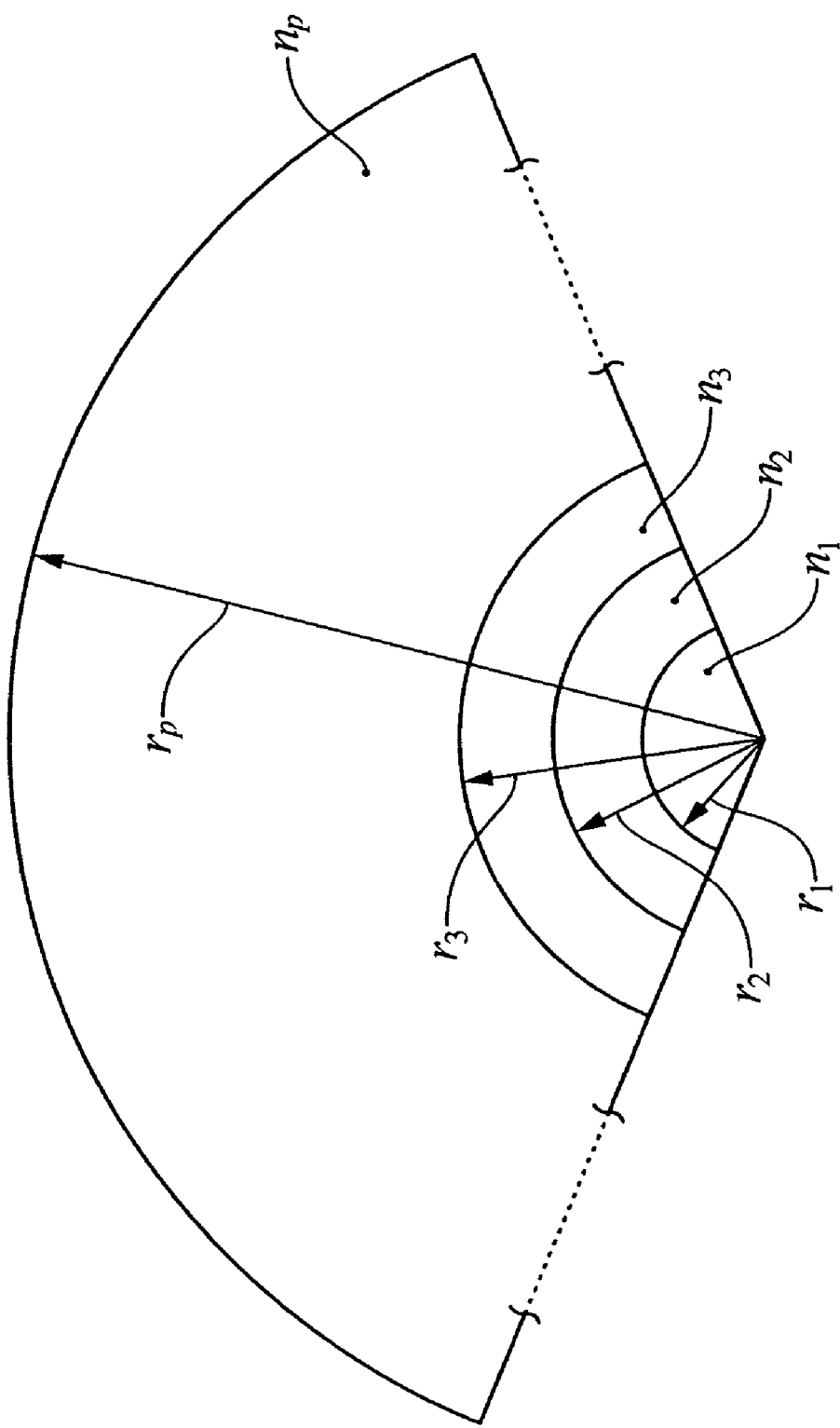
FIG. 2b is a diagram showing surfaces and corresponding radii of a catadioptric imaging system.
Figure 2C:
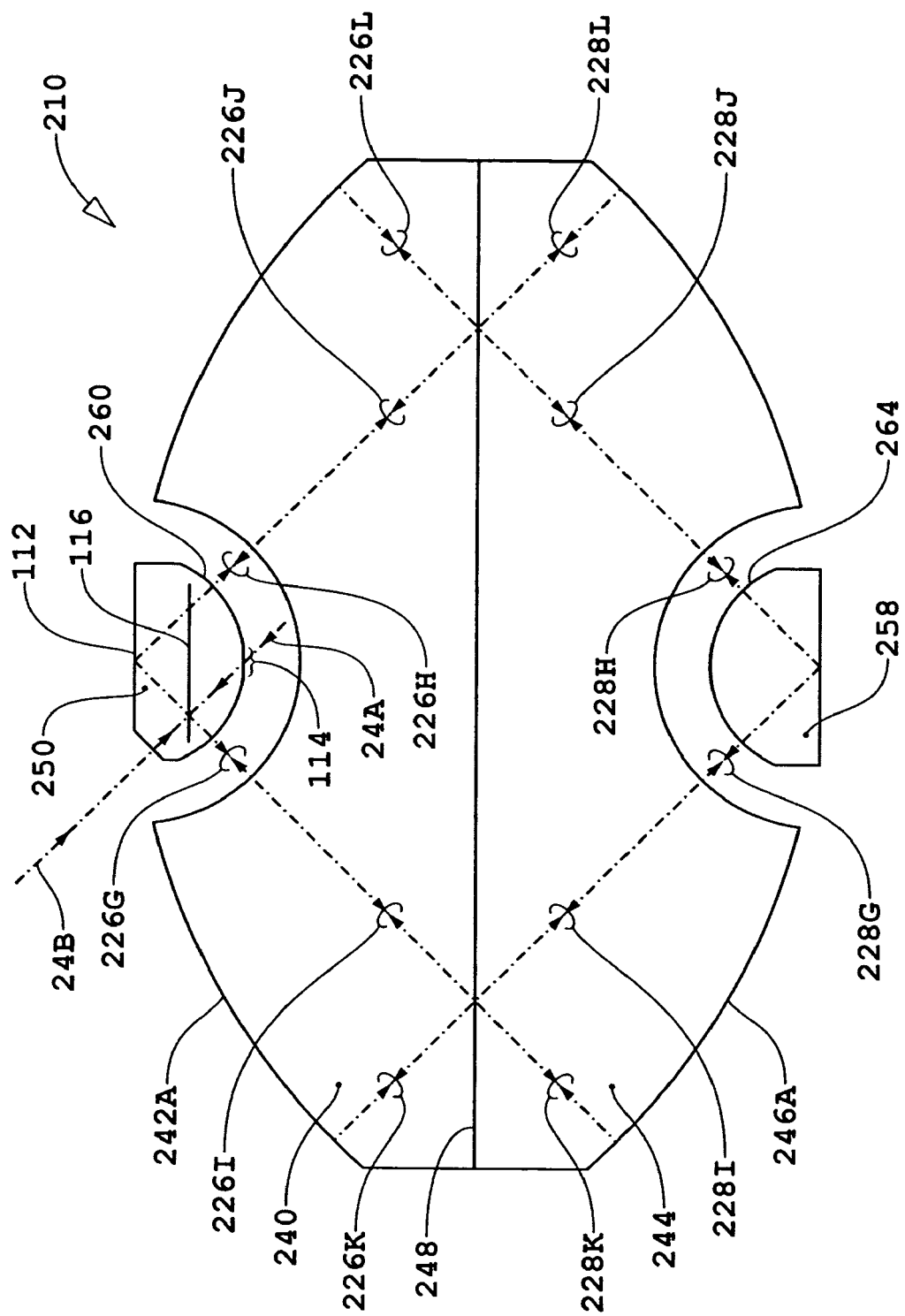
FIG. 2c is a diagram an astigmatic catadioptric imaging system and a beam-splitter system for introducing measurement and reference beams into an interferometric metrology system.

The use of slit-array 114 and non-polarizing beam-splitter 116 are also shown in FIG. 2*c*.

Catadioptric imaging system 100 comprises a section of catadioptric imaging system 210 shown schematically in FIG. 2*a* that corresponds to the section shown in FIG. 1*d*. Elements of catadioptric imaging system 210 shown in FIG. 2*a* comprise two different media in order to generate an achromatic anastigmat. Catadioptric imaging system 210 comprises catadioptric elements 240 and 244, beam-splitter 248, concentric lenses 250 and 254, and plano-convex lenses 256 and 258. Surfaces 242A and 246A are convex spherical surfaces with nominally the same radii of curvature and the respective centers of curvature of surfaces 242A and 246A are conjugate points with respect to beam-splitter 248. Surfaces 242B and 246B are concave spherical surfaces with nominally the same radii of curvature. The centers of curvature of surfaces 242B and 246B are the same as the centers of curvature of surfaces 246A and 242A, respectively.

The centers of curvature of the surfaces of concentric lens 250 and plano-convex lens 256 are nominally the same as the center of curvature of surfaces 242B and 246A. The centers of curvature of the surfaces of concentric lens 254 and plano-convex lens 258 are nominally the same as the center of curvature of surfaces 242A and 246B. The radii of curvature of surfaces 260 and 264 are nominally the same and the radii of curvature of surfaces 262 and 266 are nominally the same. There may be a small gap between the convex surface and corresponding concave surface of lenses 256 and 250, respectively, and there may be a corresponding small gap between the convex surface and corresponding concave surface of lenses 258 and 254, respectively.

The sagittal field of catadioptric imaging system 210 is a flat field and the tangential field is also a flat field for a certain object field when the Petzval sum is zero, i.e.

$$2\sum_{j=1}^{p-1} \left( \frac{1}{n_j} - \frac{1}{n_{j+1}} \right) \frac{1}{r_j} + \frac{1}{n_p} \frac{2}{r_p} = 0 \quad (15)$$

where $r_j$ is the radius of curvature of surface j, $r_p$ is the radius of curvature of the mirror surface, and $n_j$ is the index of refraction of the media located on the beam incidence side of surface j such as shown diagrammatically in FIG. 2b. The condition for the generation of an achromatic anastigmat at wavelength $\lambda_c$ is accordingly given by the equation $$\partial \frac{\left[ 2\sum_{j=1}^{p-1} \left( \frac{1}{n_j} - \frac{1}{n_{j+1}} \right) \frac{1}{r_j} + \frac{1}{n_p} \frac{2}{r_p} \right]}{\partial \lambda} = 0. \quad (16)$$

Two considerations in the selection of the radii of curvature of surfaces 242B and 246B and surfaces 162 and 166 are the area of the system pupil function of the imaging system 210 and the size of the object field that can be effectively used with respect to image quality. The first two considerations place competing demands of the selection of the radii of curvature of surfaces 242B and 246B and surfaces 162 and 166. Third and fourth considerations are with respect to the conditions set out in Equations (15) and (16). A fifth consideration in the selection of the media of the lenses of imaging system 210 is the transmission properties of the media for the range of wavelengths to be used in an end use application.

For an example of an achromatic anastigmat design for deep UV operation, the media of elements 240, 244, 256, and 258 is selected as $CaF_2$ and the media of concentric lenses 252 and 254 is selected as a UV grade fused silica. Other parameters of the example achromatic anastigmat design such as the radii of curvature of surfaces are listed in Table 1 for $\lambda_c=250$ nm. With this choice of media, the operation range is down to 170 nm. For the achromatic anastigmat design parameters listed in Table 1, the contribution of geometric ray tracing effects is $\leq 40$ nm for an object field of 1.5 mm in diameter and a numerical aperture NA=0.970 in the object space just outside of the plane surface of plano-convex lens 258.

TABLE 1

Achromatic Anastigmat Design for $\lambda_c$ = 250 nm

| Media | j | $n_j$ | $r_j$ (mm) |
|---|---|---|---|
| $CaF_2$ | 1 | 1.467297 | 3.600 |
| Fused Silica | 2 | 1.507446 | 9.256 |
| Vacuum | 3 | 1 | 18.000 |
| $CaF_2$ | 4 | 1.467297 | 50.000 |

A variant of catadioptric imaging system 210 is shown in FIG. 2c wherein catadioptric imaging system 110 is an anastigmat that is not achromatic. The media of elements 140 and 144 may comprise $CaF_2$, $BaF_2$, or $SrF_2$ for work down to 140 nm and UV grade fused silica for operation to 180 nm. The respective radii of curvature for anastigmat design at $\lambda=250$ nm using $CaF_2$ are listed in Table 2. For the anastigmat design listed in Table 2, the contribution of geometric ray tracing effects is $\leq 40$ nm for an object field of 1.5 mm and a numerical aperture NA=0.970 in the object space just outside of the plane surface of plano-convex lens 258.

TABLE 2

Anastigmat Design for $\lambda$ = 250 nm

| Media | j | $n_j$ | $r_j$ (mm) |
|---|---|---|---|
| $CaF_2$ | 1 | 1.467297 | 7.950 |
| Air | 2 | 1 | 12.000 |
| $CaF_2$ | 3 | 1.467297 | 50.000 |

The respective radii of curvature for anastigmat design at $\lambda=250$ nm using fused silica are listed in Table 3. For the anastigmat design listed in Table 3, the contribution of geometric ray tracing effects is $\leq 40$ nm for an object field of 1.5 mm and a numerical aperture NA=0.970 in the object space just outside of the plane surface of plano-convex lens 258.

TABLE 3

Anastigmat Design for $\lambda$ = 250 nm

| Media | j | $n_j$ | $r_j$ (mm) |
|---|---|---|---|
| Fused Silica | 1 | 1.467297 | 7.950 |
| Air | 2 | 1 | 12.000 |
| Fused Silica | 3 | 1.467297 | 50.000 |

Intrinsic birefringence of $SrF_2$ is less than the intrinsic birefringence of $CaF_2$ and $BaF_2$ at 140 nm. However, the intrinsic birefringence of any one of the three crystalline materials can be accommodated in the catadioptric imaging system 100 since only an azimuthal section of the lens elements are used and that section can be selected to significantly reduce the effects of intrinsic birefringence, e.g., with the [111] axis of the crystal aligned parallel to the optic axis of catadioptric imaging system 10 and the [110] axis of the crystal aligned parallel to the plane of FIG. 2a.

Also shown in FIG. 2c are measurement beam 24A and reference beam 24B, slit-array 114, and beam-splitter 116. The description of the generation of measurement beam 24A and reference beam 24B and the description of slit-array 114 and beam-splitter 116 are the same as the description given for the same element numbers shown in FIG. 1f.

Figure 2D:
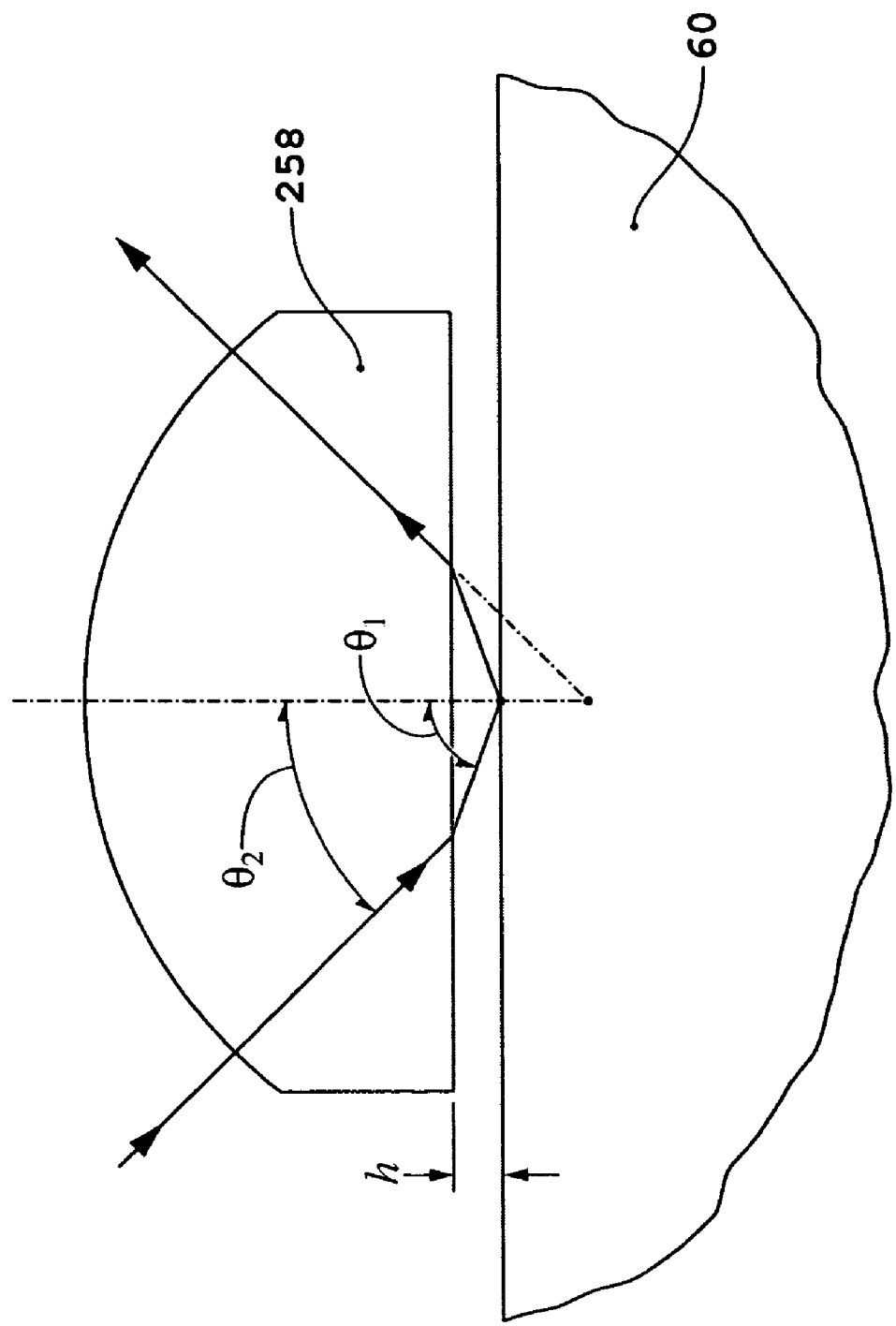
FIG. 2d is a schematic diagram of a section of a catadioptric imaging system located near a measurement object.
Figure 2E:
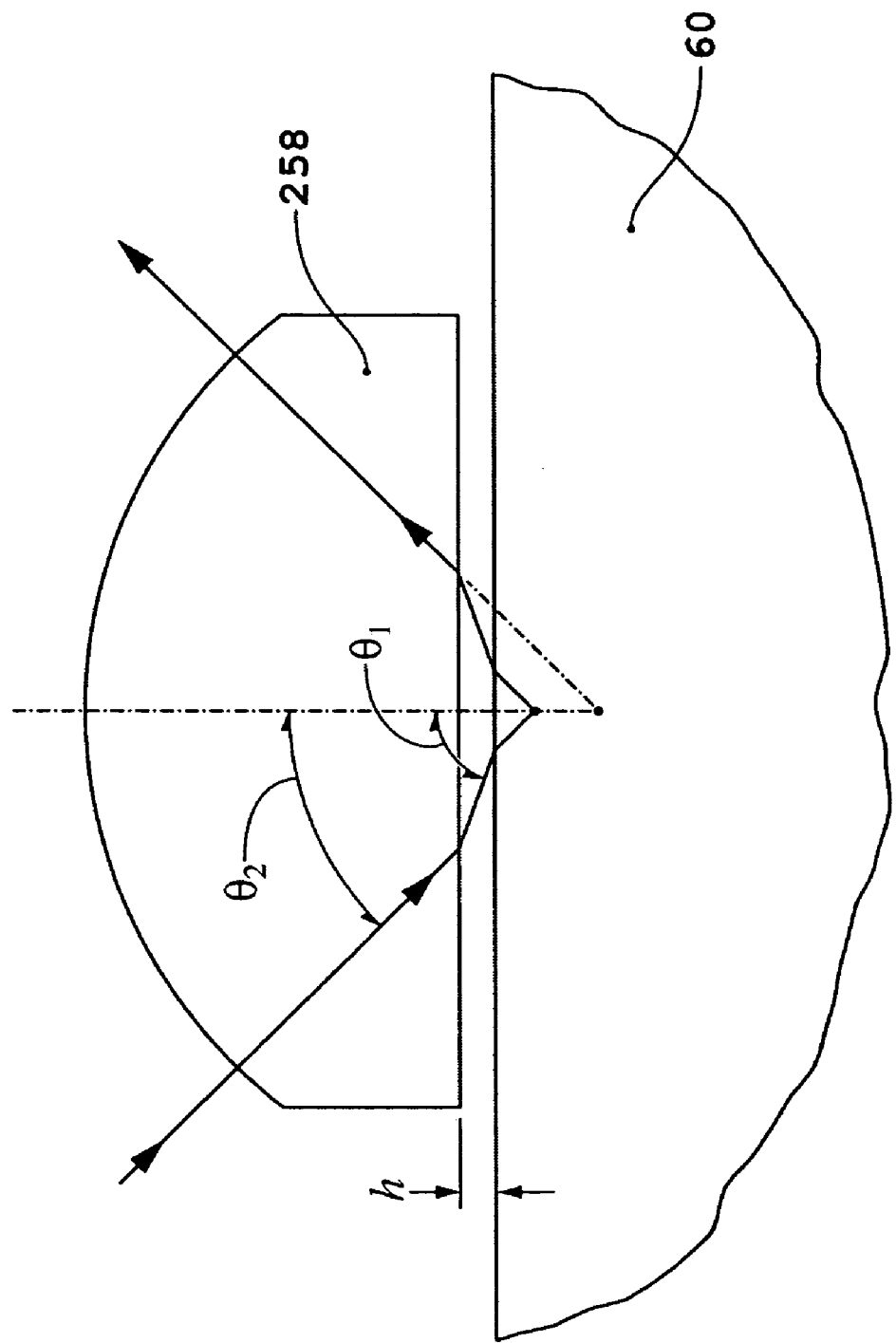
FIG. 2e is a schematic diagram of a section of a catadioptric imaging system located near a measurement object and imaging an interior section of the measurement object.

Another form of catadioptric imaging system that may be used for catadioptric and catoptric imaging system 100 is the catadioptric imaging system such as described in cited U.S. patent application Ser. No. 10/866,010 (ZI-52). The location of the object plane of catadioptric imaging system 210 is outside of plano-convex lens 258 and on the surface of substrate 60 which is shown diagrammatically in FIG. 2d. The separation of the plane surface of plano-convex lens 258 and the surface of substrate 60 is h. The object plane of catadioptric imaging system 210 may also be located in the interior of substrate 60 which is shown diagrammatically in FIG. 2e. Also the space between plano-convex lens 258 and the surface of substrate 60 may be filled with a coupling fluid to increase the numerical aperture of the measurement beam at substrate 60 and achieve the benefits of emersion coupling. The coupling fluid may be an index matching fluid to reduce aberrations generated by index of refraction mismatch at the plane surface of plano-convex lens 258.

The measurement beams at substrate 60 may be in the form of evanescent fields. The evanescent fields are generated by selecting the angle of incidence $\theta_2$ (see FIG. 1*d*) of the measurement beams at the plane surface of plano-convex lens 258 to be greater than that required to produce total internal reflection and the separation $h \leq \lambda/4$ such as described in cited U.S. Pat. No. 6,445,453 (ZI-14), U.S. patent application Ser. No. 10/866,010 (ZI-52). The angle of incidence may be selected by the relative locations of apertures used in a mask such as mask 114B of the third embodiment.

The measurement beams at substrate 60 may be in the form of near-fields when an array of transmitting sub-wavelength apertures is located on the plane surface of plano-convex lens 258 and the separation $h \leq \lambda/4$ such as described in cited U.S. Pat. No. 6,445,453 (ZI-14).

An advantage of the catadioptric imaging system 210 is that as a consequence of the spherical aberration introduced by transmission through plane surfaces, the effective angle of incidence $\theta_1$ (see FIG. 2*d*) can be scanned by introducing a scan in h.

For those end use applications where compensation is required for the spherical aberration introduced by transmission through plane surfaces, procedures may be use such as described in commonly owned U.S. patent application Ser. No. 10/771,785 (ZI-44), entitled "Compensation for Effects of Mismatch in Indices of Refraction at a Substrate-Medium Interface in Confocal and Interferometric Confocal Microscopy" by Henry A. Hill and the contents of which are incorporated herein by reference.

The description of imaging system 100 is continued with reference to FIG. 1*d*. Lens sections 40 and 44 are pie sections of lens 240 and 244 shown in FIG. 2*a*. Lens elements 250, 256, 254, and 258 in FIG. 1*d* are the same elements lens elements 250, 256, 254, and 258 in FIG. 2*a*. Convex lens 52 has a center of curvature the same as the center of curvature of convex lens 250. Convex lenses 250 and 52 are bonded together with pinhole beam-splitter 12 in between. The position of pinhole array beam-splitter 12 is shown in FIG. 1*d*. The pattern of pinholes in pinhole array beam-splitter is chosen so that the image of pinhole beam-splitter 12 on detector 70 to match the pixel pattern of detector 70. An example of a pattern is a two dimensional array of equally spaced pinholes in two orthogonal directions. The pinholes may comprise circular apertures, rectangular apertures, or combinations thereof such as described in commonly owned U.S. patent application Ser. No. 09/917,402 (ZI-15) entitled "Multiple-Source Arrays for Confocal and Near-field Microscopy" by Henry A. Hill and Kyle Ferrio of which the contents thereof are incorporated herein in their entirety by reference. The pinholes may also comprise microgratings such as described in cited U.S. patent application Ser. No. 10/816,180, filed Apr. 1, 2004, entitled "Apparatus and Method for Joint Measurement Of Fields Of Scattered/Reflected or Transmitted Orthogonally Polarized Beams By An Object In Interferometry," (ZI-50). A non-limiting example of a pinhole array for pinhole array beam-splitter 12 is shown in FIG. 1*e* having a spacing between pinholes of b with aperture size a.

A second embodiment is described for the joint measurement of the conjugated quadratures of fields of complimentary oblique measurement beams reflected/scattered by Porro type prism elements of features of a measurement object. The complimentary oblique measurement beams correspond to two measurement beams that have angles or average angles of incidence that are equal in magnitude but opposite in sign. The information obtained for each of the two measurement beams is the same as the information obtained respectively by using the first embodiment of the present invention with the measurement object in a non-rotated and in a rotated orientation. The rotation axis for changing the orientation of the measurement object is parallel to the optic axis of the interferometric metrology system shown in FIG. 1*c*. The difference between the second embodiment and the use of the first embodiment with the measurement object in a non-rotated and in a rotated orientation is that the information obtained for the two different orientations of the measurement object is obtained sequentially in the case of the first embodiment and is obtained jointly in the case of the second embodiment.

The second embodiment comprises the apparatus of embodiments described in cited commonly owned U.S. patent application Ser. No. 10/816,172 (ZI-51) with certain modifications. The certain modifications have to do with the introduction of the measurement and reference beams to the interferometry metrology system of the second embodiment and the use of a phase-shifter 46C shown in FIG. 1*e* of cited U.S. patent application Ser. No. 10/816,172 (ZI-51). The description of the use of phase-shifter 46C to separate the forward and backscattered components of measurement beams is the same as the corresponding portions of descriptions given in cited U.S. patent application Ser. No. 10/816,172 (ZI-51).

The modification of the introduction of the measurement beam corresponds to the introduction of two complimentary oblique measurement beams comprising two measurement beams that have angles or average angles of incidence that are equal in magnitude but opposite in sign at slit-array 114 shown in FIGS. 1*f* and 2*c* and overlap at slit-array 114. The modification of the introduction of the reference beam corresponds to the introduction of two complimentary oblique reference beams comprising two reference beams that have angles or average angles of incidence that are equal in magnitude but opposite in sign at beam-splitter 116 shown in FIGS. 1*f* and 2*c* and overlap at pinhole array beam-splitter 12.

The remaining description of the certain modifications of the second embodiment is the same as corresponding portions of the description given herein for the certain other modifications of the third embodiment. The remaining description of the second embodiment is the same as corresponding portions of the description given for the first embodiment herein.

A variant of the second embodiment obtains the information of the second embodiment in a non-joint manner. The variant of the second embodiment comprises the apparatus of the second embodiment with a set of shutters without phase-shifter 46C. The set of shutters are configured to shutter the input measurement and reference beams and the forward scattered measurement beams. The variant of the second embodiment corresponds to using the first embodiment with the measurement object in a non-rotated and in a rotated orientation.

A third embodiment is described for the measurement of the conjugated quadratures of fields of complimentary oblique measurement beams reflected/scattered by Porro type prism elements of measurement object features and/or of non-oblique measurement beams that are reflected/scattered by the measurement object. The third embodiment obtains information about the measurement object using one or more of two complimentary oblique measurement beams and non-oblique measurement beams with a single interferometric metrology system. The complimentary oblique measurement beams correspond to two measurement beams that have angles or average angles of incidence that are equal in magnitude but opposite in sign. The non-oblique measurement beams have a nominally zero angle of incidence at the measurement object and may comprise for example two complimentary oblique measurement beams simultaneously. The corresponding measured conjugated quadratures comprise conjugated quadratures of measured fields of the forward reflected/scattered and backscattered non-oblique measurement beam by the measurement object.

The information obtained for each of the two complimentary oblique measurement beams is the same as the information obtained respectively by using the first embodiment with the measurement object in non-rotated and in a rotated orientations. The information obtained with the non-oblique measurement beam exhibits sensitivity to lateral shifts of the measurement object that is different from the sensitivity of the information obtained with either of the two complimentary oblique measurement beams to lateral shifts of the measurement object. The information obtained with the non-oblique measurement beams is used for example for defect detection and surface profiling and may be the same as obtained from differential or non-differential interferometric microscopy systems such as described in cited U.S. patent applications Ser. No. 10/778,371 (ZI-40), Ser. No. 10/782,057 (ZI-41), Ser. No. 10/782,058 (ZI-42), Ser. No. 10/816,180 (ZI-50), and Ser. No. 10/816,172 (ZI-51) depending upon the specific imaging system used for 10 of FIG. 1a.

The third embodiment comprises the same apparatus of certain of the embodiments described in cited U.S. Provisional Patent Application No. 60/460,129 (ZI-51) and U.S. patent application Ser. No. 10/816,172 (ZI-51) with certain other modifications such as shown schematically in FIGS. 1i and 1j. The certain other modifications are with respect to the introduction of the reference and measurement beams to the interferometric metrology system of the third embodiment and with respect to spatial filtering of the reference beam, the complimentary oblique and the non-oblique measurement beams, and the fields of the two complimentary oblique measurement beams and the non-oblique measurement beam forward reflected/scattered and/or backscattered by the measurement object. The spatial filtering determines which type of information is being detected by a given pixel of detector 70, e.g. information corresponding to a non-oblique measurement beam, to an oblique measurement beam with a given non-zero angle of incidence on the measurement object, or an complimentary oblique measurement beam with a complimentary non-zero angle of incidence at the measurement object.

The interferometer system of the third embodiment is the same as the interferometer system of the first embodiment shown in FIG. 1c except with respect to the first imaging system 100 and to the certain other modifications for the introduction of the reference and measurement beams and the spatial filtering. First imaging system 100 for the third embodiment comprises a catadioptric imaging system such as shown as imaging system 200 in FIG. 1i and also such as corresponding catadioptric imaging systems described in cited U.S. patent application Ser. No. 10/816,172 (ZI-5 I).

The description of the imaging properties of catadioptric imaging system 200 is broken into two different descriptions with one description of the system functioning as imaging system 100 of the first embodiment for complimentary oblique measurement beams and with a second description of the system functioning as an imaging system for non-oblique reference and measurement beams. The properties of spatial filters or masks 112B and 114B (see FIG. 1j) determine which of the two descriptions is applicable for a given pinhole of pinhole array beam-splitter 112A. Pinhole array beam-splitter 112A functions as a beam-splitter for combining reference and measurement beams of an interferometer and the description of this function is the same as the corresponding portion of the description given for the imaging properties of catadioptric imaging system 10 in cited U.S. patent application Ser. No. 10/765,229 (ZI-45).

Input beam 24 comprises spatially separated reference and measurement beams 1024 and 1026, respectively, (see FIG. 1b) with the same directions of propagation. Reference beam 1024 is redirected relative to the direction of propagation of measurement beam 1026 by mirror 154A as shown in FIG. 1i. Reference and measurement beams 1024 and 1026 are incident on imaging system 200 wherein reference beam components of output beam 30A and 30B are generated and a measurement beam components of beams 126A and 126B are generated. The measurement beam components 126A and 126B are imaged as components of beams 128A and 128B to an array of image spots in an image plane close to or on substrate 60. A portion of the components of beams 128A and 128B incident on substrate 60 are reflected and/or scattered as return measurement beam components of beams 128A and 128B. Return measurement beam components of beams 128A and 128B are imaged by catadioptric imaging system 200 in the plane of pinhole array beam-splitter 112A and a portion thereof is transmitted as return measurement beam components of output beams 30A and 30B.

Figure 1H:
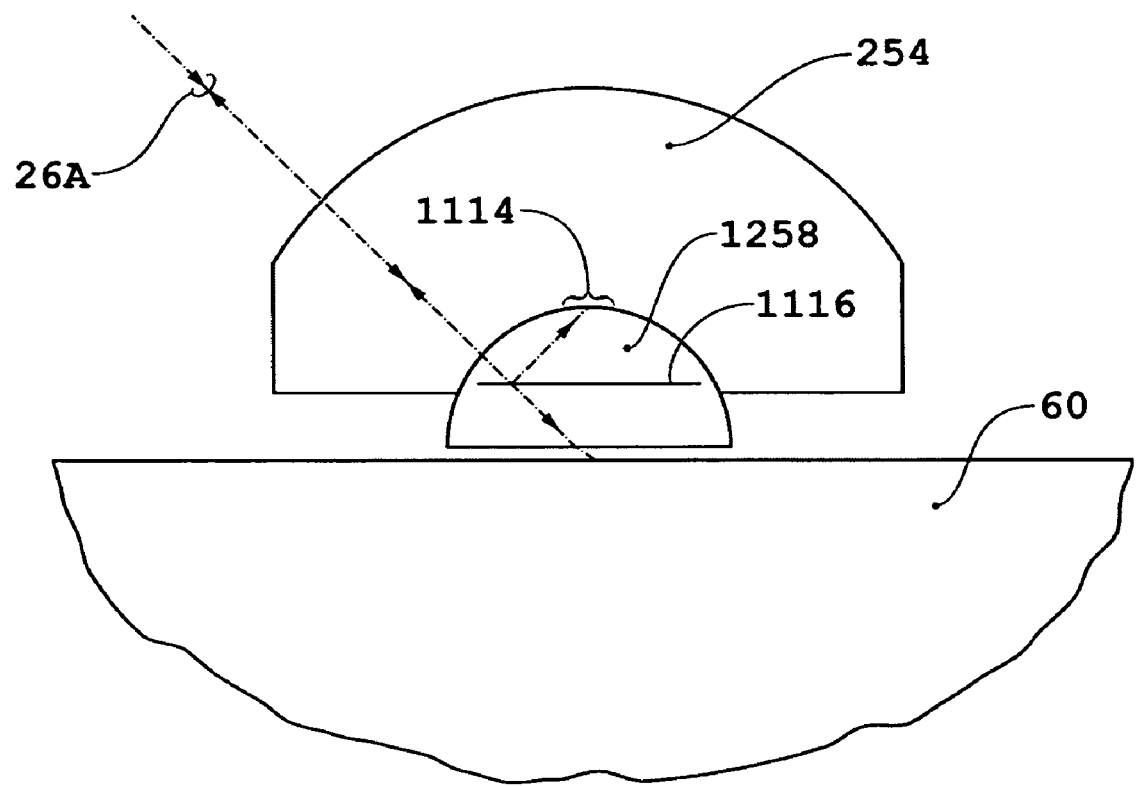
FIG. 1h is a diagram of a beam-splitter system for introducing measurement and reference beams into an interferometric OCDR system.
Figure 1I:
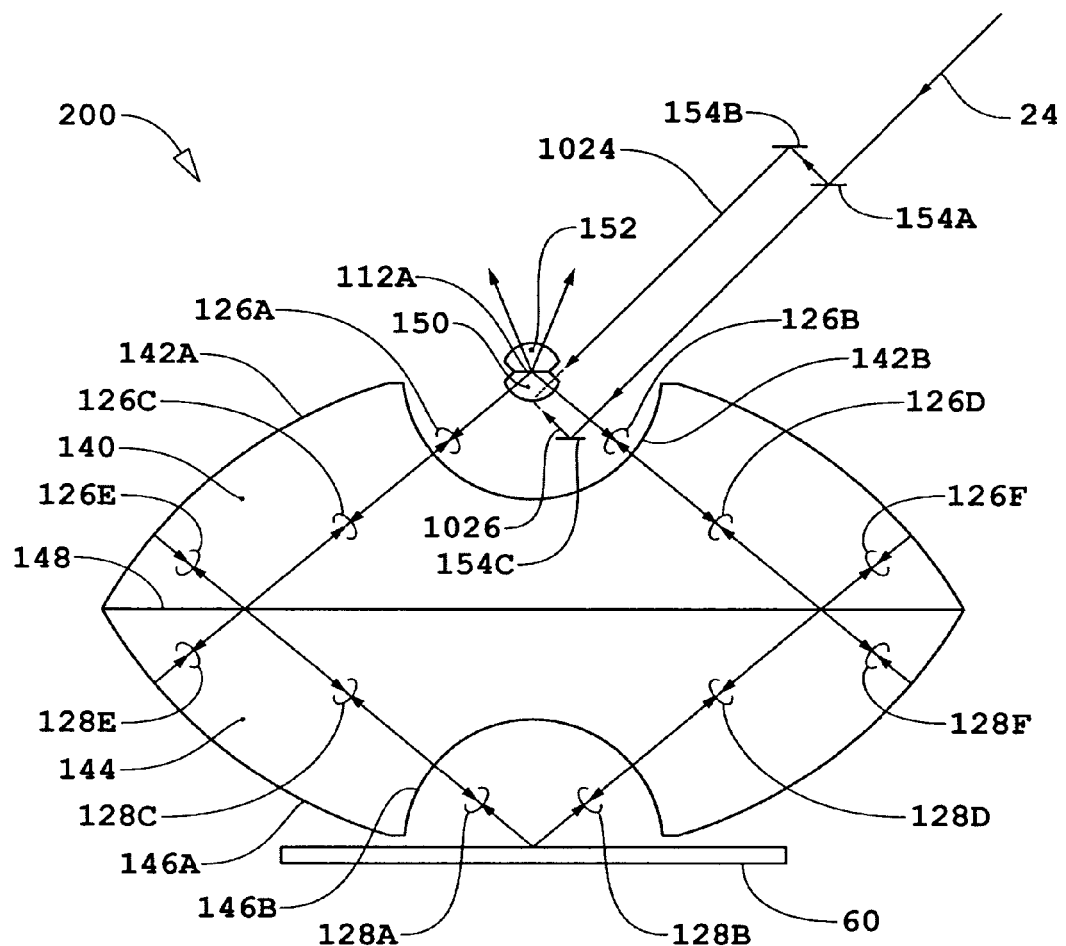
FIG. 1i is a schematic diagram of a catadioptric imaging system.
Figure 1J:
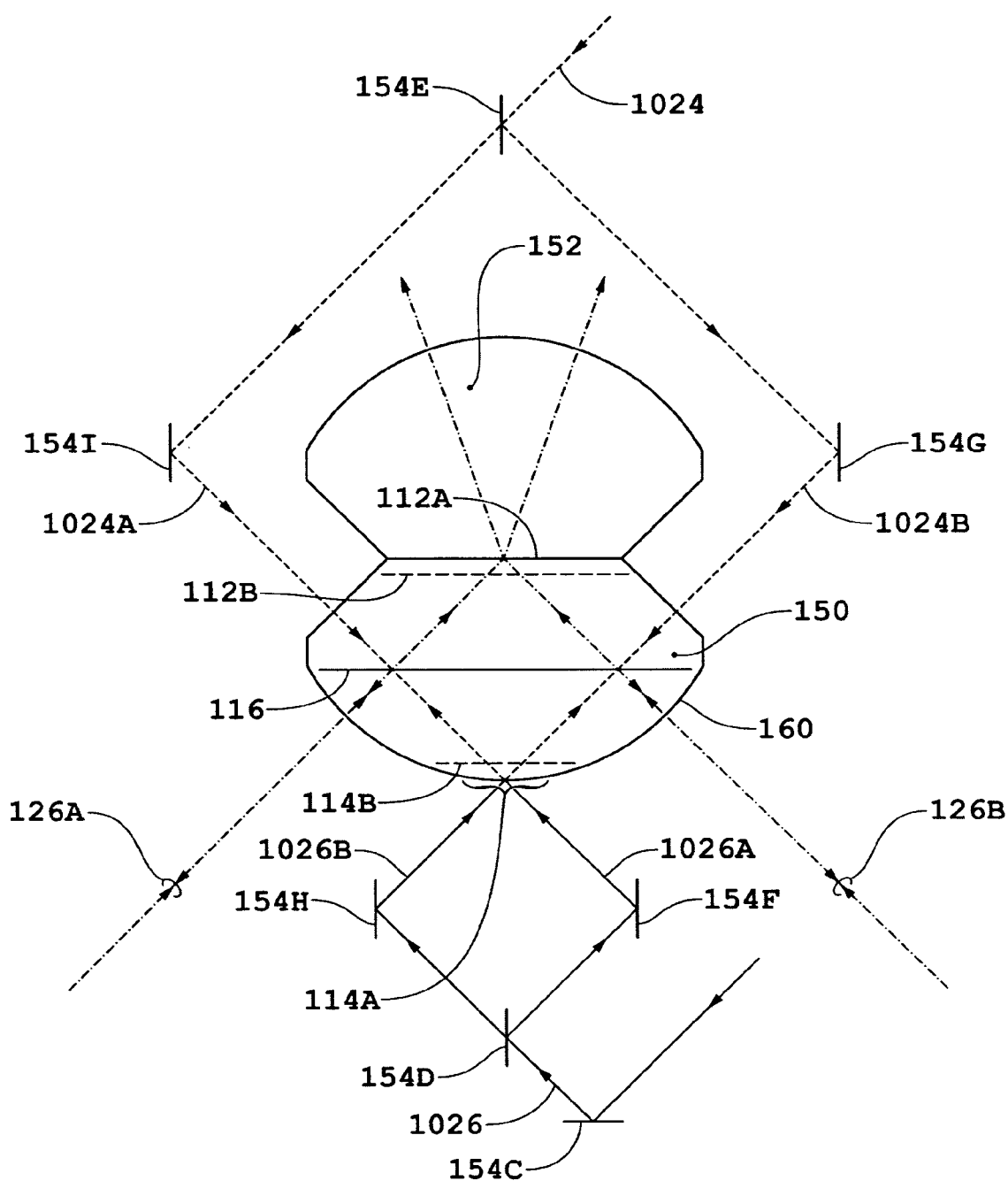
FIG. 1j is a diagram of a system for introducing measurement and reference beams into an interferometric metrology system.

The certain other modifications for the introduction of the measurement beam corresponds to the introduction of two complimentary oblique measurement beams comprising two measurement beams that have angles or average angles of incidence that are equal in magnitude but opposite in sign at slit-array 114A shown in FIG. 1j and which overlap at slit-array 114A. The modification for the introduction of the reference beam corresponds to the introduction of two complimentary reference beams comprising two reference beams that have angles or average angles of incidence that are equal in magnitude but opposite in sign at beam-splitter 116 shown in FIG. 1j and overlap at pinhole array beam-splitter 112A.

With reference to FIG. 1j, first and second portions of measurement beam component 1026 of input beam 24 are reflected and transmitted, respectively, by non-polarizing beam-splitter 154D as measurement beams 1026A and 1026B, respectively, wherein measurement beams 1026A and 1026B have been reflected by mirrors 154F and 154H, respectively. Measurement beams 1026A and 1026B are incident on the slit-array 114A with angles of incidence that have the same magnitude and opposite signs. A portion of measurement beams 1026A and 1026B incident on slit-array 114A is transmitted as an array of diffracted measurement beams.

Slit-array 114A comprises slits 64A which are at conjugate locations with reference to beam-splitter 116 of pinholes 62 of pinhole array 112A. The apertures of mask 114B are at corresponding locations to pinholes of pinhole array 112A that are at conjugate locations with reference to beam-splitter 116 of apertures of mask 112B as shown schematically in FIGS. 1j and 1k. The spacing between mask 112B and pin-hole array 112A and the spacing between mask 114B and slit-array 114A is in each case g as shown in FIG. 1k. The apertures 2012 and 2016 of mask 112B, slits 64A of slit-array 114A, and apertures 2112 and 2116 of mask 114B are used to generate the two complimentary oblique reference and measurement beams and the apertures 64B of slit-array 114A and apertures 2014 and 2114 of the masks 112B and 114B, respectively, are used to generate the non-oblique reference and measurement beams. The function of generation of the two complimentary oblique reference and measurement beams and generation of the non-oblique reference and measurement beams can be achieved for example with g=b/4 such as shown schematically in FIG. 1k. The description of slits of slit-array 114A is the same as the corresponding portion of the description given for slits of slit-array 114 of the first embodiment. Spatial filters or masks 112B and 114B comprise masks that have sections which transmit beams and sections that do not transmit beams as shown schematically in FIG. 1k and are used to define in part the pupil functions of imaging system 200 for respective pinholes of pinhole array beam-splitter 112A. In particular, apertures 2014 and 2114 permit beams to pass from a respective pinhole or slit that are associated with both positive and negative values of pupil coordinate ξ while apertures 2012, 2112, 2016, and 2116 permit beams to pass from a respective pinhole or slit that are associated with either a positive and a negative value of pupil coordinate ξ but not both.

The combination of slit array 114A and mask 114B generates three types of measurement beams that are directed onto corresponding spots on the surface of the object. A first type of measurement beam, resulting from slit 64A in combination with aperture 2112, is directed by the imaging system onto a corresponding spot on the object along a first direction or average direction that is oblique to the surface of the object. A second type of measurement beam, resulting from slit 64A in combination with aperture 2116, is directed by the imaging system onto a corresponding second spot (e.g. neighboring spot) on the object along a second direction or average direction that is also oblique to the surface of the object but is complimentary to the first direction (i.e., the second measurement beam propagates relative to the surface of the object in a direction that is opposite to the first direction). A third type of measurement beam, resulting from slit 64B in combination with aperture 2114, is directed by the imaging system onto a corresponding third spot on the object along a third direction or average direction that is non-oblique to the surface of the object (i.e., its average direction is perpendicular to the surface of the object). This third beam is generated by simultaneously directing a beam of the first type and a beam of the second type onto the corresponding third spot. With reference to FIG. 1i, a measurement beam of the first type would be measurement beam 128A by itself, a measurement beam of the second type would be measurement beam 128B by itself, and a measurement beam of the third type would be measurement beam 128A in combination with measurement beam 128B. Thus, with this implementation all three types of measurements can be simultaneously made on the surface of the object and with one scan sufficient data can be collected to accurately locate the features in the x-y plane which is a plane parallel to the surface of the object (e.g. by removing a vertical component that would impact the x-y location information obtained from the oblique measurement beams).

In a similar way, the combination of slit array 112A and mask 112B operate on the return measurement beams to spatially filter them so that one slot passes only the return measurement beam from a corresponding oblique measurement beam, a second slot passes only the return measurement beam from a corresponding oblique measurement beam that complimentary to the first-mentioned measurement beam, and a third slot passes both return measurement beams (or the non-oblique measurement beam).

Continuing with reference to FIG. 1j, first and second portions of the reference beam component 1024 of input beam 24 are transmitted and reflected, respectively, by non-polarizing beam-splitter 154E as reference beams 1024A and 1024B wherein reference beams 1024A and 1024B have been reflected by mirrors 154I and 154G, respectively. Reference beams 1024A and 1024B are incident on non-polarizing beam-splitter 116 with angles of incidence that have the same magnitude and of opposite signs.

The angles of incidence of the reference beam components incident on pinhole array beam-splitter 112A are selected to meet the condition specified with respect to the general property described following Equation (10) herein. The general property has to do with the absence of a x or lateral dependence in the interference cross-term between the reference beam and the reflected/scattered complimentary oblique measurement beams from a given Porro type prism element in the electrical interference signal values.

The first description of the propagation of two complimentary oblique measurement beams through imaging system 200 that are portions of the diffracted measurement beams transmitted by apertures of mask 114B and reflected by non-polarizing beam-splitter 116 and the description of the reflected/scattered measured beams through imaging system 200 and transmitted by non-polarizing beam-splitter 116 and apertures of conjugate mask 112B is the same as the corresponding portions of the descriptions given with respect to the first embodiment for the propagation of the measurement beams and the reflected/scattered measurement beams through imaging system 100.

Continuing with the second description of the imaging properties of imaging system 200, reference is made to FIG. 1i. Catadioptric imaging system 200 comprises catadioptric elements 140 and 144, beam splitter 148, and convex lens 150. Surfaces 142A and 146A are convex spherical surfaces with nominally the same radii of curvature and the respective centers of curvature of surfaces 142A and 146A are conjugate points with respect to beam splitter 148. Surfaces 142B and 146B are concave spherical surfaces with nominally the same radii of curvature. The centers of curvature of surfaces 142B and 146B are the same as the centers of curvature of surfaces 146A and 142A, respectively. The center of curvature of convex lens 150 is the same as the center of curvature of surfaces 142B and 146A.

The radius of curvature of surface 146B is selected so as to minimize the loss in efficiency of the imaging system 200 and to produce a working distance for imaging system 200 acceptable for an end use application. The radius of curvature of surface 160 of convex lens 150 is selected so that the off-axis aberrations of the catadioptric imaging system 200 are compensated. The description of the selection procedure is the same as corresponding portions of the description given herein with respect to imaging systems shown in FIGS. 1d and 2a. The medium of elements 140 and 144 may be for example fused silica or commercially available glass such as SF11. The medium of convex lens 150 may be for example fused silica, YAG, or commercially available glass such as SF11. An important consideration in the selection of the medium of elements 140 and 144 and convex lens 150 will the transmission properties for the frequencies of beam 24. Examples of solutions are given in cited U.S. patent application Ser. No. 10/866,010 (ZI-52) [see Tables 2 and 3 and related discussion with respect to FIG. 2f of cited application Ser. No. 10/866,010].

Convex lens 152 has a center of curvature the same as the center of curvature of convex lens 150. Convex lenses 150 and 152 are bonded together with pinhole beam-splitter 112A in between. Pinhole array beam-splitter 112A is the same as pinhole array beam-splitter 112 shown in FIG. 1e. The pattern of pinholes in pinhole array beam-splitter is chosen to match the requirements of an end use application. An example of a pattern is a two dimensional array of equally spaced pinholes in two orthogonal directions. The pinholes may comprise circular apertures, rectangular apertures, or combinations thereof such as described in cited U.S. patent application Ser. No. 09/917,402 (ZI-15). The spacing between pinholes of pinhole array beam-splitter 112A is the same as shown in FIG. 1e as b with aperture size a. An advantage of the third embodiment is that information can be obtained about the measurement object using one or more of the two complimentary oblique measurement beams and non-oblique measurement beams with a single interferometric metrology system without rotation of either the measurement object or the interferometric metrology system.

In the third embodiment, the information obtained about the location of feature on a measurement object in a plane parallel to the surface of the measurement object is obtained operating in a scanning mode as with other embodiments of the present invention. The statistical and systematic errors in the phases of the measured conjugated quadratures obtained when operating in a scanning mode are reduced as a consequence of using the bi-homodyne detection method or variants thereof. The statistical and systematic errors are also reduced as a consequence of the detection of information about a large array of image spots on a substrate simultaneously as a consequence of using a detector comprising a large array of pixels. This feature leads to reduced sensitivity to vibrations and a high throughput.

The statistical and systematic errors obtained in the third embodiment are further reduced as a consequence of the design of the pinhole array 112A, the slit array 114A, and the masks 112B and 114B, respectively, to permit the simultaneous acquisition of information using oblique measurement beams, complimentary oblique measurement beams, and non-oblique measurement beams. The information obtained with the non-oblique measurement beams is used to measure the height profile of a surface of a measurement object and in particular the height of features in or on the measurement object, to identify the presence and location of defects, and to detect changes in the vertical position and angular orientation of the measurement object about axes of rotation parallel to the surface of the measurement object that occur during the scanning of the measurement object.

The detected changes in the vertical position and angular orientation of the measurement object are used to correct the measured arrays of conjugated quadratures obtained for the oblique and complimentary oblique measurement beams for changes in the vertical position and angular orientation of the measurement object that occur during the scanning of the measurement object.

The measured height profile of the surface or height of a feature is used in conjunction with the arrays of measured conjugated quadratures obtained for the oblique and complimentary oblique measurement beams to obtain information about the location of features on the surface of the measurement object in a plane parallel to the surface of the measurement object.

In the third embodiment and in other embodiments, the conjugated quadratures of fields of reflected/scattered measurement beams may be measured as a function of the angle of incidence of the measurement beams at the measurement object and/or as a function of the angle of reflection or scattering of the reflected/scattered measurement beam. The angles of incidence and the angles of reflection or scattering are selected for example by the design of the relative locations apertures in the masks 114B and 112B, respectively. Thus, with one set of masks it is possible to generate measurement beams having different average angles of incidence, with each of the different angles of incidence corresponding to a different part of the mask. Also the range in angles of incidence and the range in the angles of reflection or scattering for a given pixel of the detector are selected for example by the design of the sizes of the apertures in the masks 114B and 112B, respectively. Thus, with one set of masks it is also possible to generate measurement beams having different ranges of angles of incidence, with each of the different ranges of angles of incidence corresponding to a different part of the mask. Accordingly, the information about the two different angular dependent properties of the measured conjugated quadratures is obtained simultaneously with corresponding benefits.

A fourth embodiment is described for the joint measurement of the conjugated quadratures of fields of complimentary measurement beams reflected/scattered by Porro type prism elements of features of a measurement object. The complimentary measurement beams correspond to two measurement beams that have orthogonal states of linear polarization. The fourth embodiment comprises the apparatus of embodiments described in cited U.S. Provisional Patent Application No. 60/459,425 (ZI-50) and U.S. patent application Ser. No. 10/816,180 (ZI-50) and the apparatus and procedures of the first embodiment described herein.

For each of the first, second, third, and fourth embodiments and variants thereof, the interferometric metrology systems may be configured in other embodiments to obtain information in the form of joint and non-joint measurements of the angular distribution of differential conjugated quadratures of reflected/scattered beams from Porro type prism elements in features of measurement objects. The other embodiments comprise the apparatus described in cited U.S. Provisional Patent Application No. 60/501,666 (ZI-54) and U.S. patent application Ser. No. 10/938,408 (ZI-54) for the acquisition of information about angular distributions.

A fifth embodiment is described for the measurement of the CDs using optical coherence-domain reflectometry (OCDR). The fourth embodiment may be described as a variant of the Mirau interferometer wherein the variant thereof is configured to measure properties of backscattered reference and measurement beams instead of beams reflected by reference and measurement objects, respectively. The apparatus of the fifth embodiment comprises the apparatus of the first embodiment except with respect to the generation of the measurement and reference beams and the source 18 and beam-conditioner 22. In the fifth embodiment, source 18 is a pulsed source with each pulse of input beam 24 produced with a short coherence length.

In the fifth embodiment, the measurement and reference beams are generated in element 1258 shown diagrammatically in FIG. 1h. Element 1258 is used in place of element 258 of the first embodiment shown in FIG. 1d. Elements 54A, 54B, and 54C shown in FIG. 1d are not used in the fourth embodiment so that input beam 24 enters interferometer 100 as 24A. Measurement beam 24A is incident on slit-array 114 and a portion thereof transmitted as an array of diffracted input beams as shown in FIG. 1f. The array of input beams is incident on non-polarizing beam-splitter 116 and a portion thereof reflected as an array of input beams forming the input beam component of beam 26A. The optical elements in FIG. 1f correspond to the optical elements in FIG. 1d.

The input beam component of beam 26A is incident on catadioptric elements 40 and 44 and exit elements 40 and 44 as an array of input beams forming the input beam component of beam 28A. As shown diagrammatically in FIG. 1h, input beam component of beam 28A is incident on non-polarizing beam splitter 1116 after transmission by lens 254 and a portion of lens 1258. First and second portions of the input beam component incident on beam-splitter 1116 are transmitted and reflected as measurement and referenced beams, respectively. The measurement beam is subsequently transmitted by the plane facet of lens 1258 and incident on measurement object 60. The reference beam is incident on reference object 1114 comprising an array of scattering sites, i.e., Porro type elements such as shown in FIG. 4a. The description of lens 1258 is other wise the same as the description of lens 258.

A portion of the measurement beam incident on measurement object 60 is backscattered by scattering sites, e.g., Porro type prism elements, and transmitted by beam-splitter 1116 to form the return measurement beam. A portion of the reference beam incident on reference object 1114 is back-scattered by the scattering sites and reflected by beam-splitter 1116 to form the return reference beam.

The return measurement and the return reference beams are imaged on pinhole array 12 by the catadioptric imaging system of interferometer 100. A portion of the return measurement and the return reference beams that are imaged on pinhole array 12 are transmitted and imaged by second imaging system 110 on pixels of detector 70 as a mixed beam. The mixed beam is detected by detector 70 by a quantum detection process to generate signal 72.

The detection of the backscattered measurement beam in the OCDR is accomplished by the method of white-light interferometry in which the location of measurement object 60 is adjustable. This method utilizes the fact that interference fringes will appear in the recombined, i.e., mixed, beam only when the difference in the optical path length between the reference and measurement paths is less than the coherence length of the beam.

Information about the height and transverse locations of the scattering sites in measurement object 60 are obtained by processing signal 72 in a manner such as used with the Mirau interferometer. For information about the transverse location of scattering sites such as formed for example by surfaces 520 and 540 of a Porro type prism element shown in FIG. 4a, the measurement object is scanned with either interferometer 100 or measurement object rotated by 180 degrees.

A variant of the fifth embodiment is configured to obtain the information of the fifth embodiment without rotation of interferometer 100 or measurement object 60 by 180 degrees. The variant of the fifth embodiment comprises the apparatus of the fifth embodiment with a set of shutters such as used in the variant of the second embodiment. The remaining portion of the description of the variant of the fourth embodiment is the same as corresponding portions of the fourth embodiment and the variant of the second embodiment.

Differential Interferometric Microscopy Systems

The differential interferometric microscopy systems of the confocal and non-confocal type are used in certain embodiments of the present invention. The embodiment that includes a differential interferometric confocal microscopy system is the same as the differential interferometric confocal microscopy system described in commonly owned U.S. patent application Ser. No. 10/816,180 (ZI-50). The differential interferometric confocal microscopy system is configured to operate in a dark field mode preferably and compares interferometrically the properties of two transversely separated sections of an open or filled feature of a mask. If the properties of the two transversely separated sections are identical as the mask is scanned, there will be no change in the measured conjugated quadratures. However, if at a certain location on the mask, there is a difference in the two interferometrically compared sections, there will be a change in the measured conjugated quadratures.

The difference in properties may be in the form of widths of the two sections, in the form of the depths of the two sections, or in the form of a particle located in one of the two sections. A difference in the two widths will generate a difference in the amplitudes of the beams scattered by the entrance plane aperture formed by the feature sections. A difference in the depths of the two sections or the presence of a particle located in one of the two sections will modify the properties of the leaky guided wave modes that are excited in the features by the respective measurement beams. The description of the excited leaky guided wave modes and the fields radiated by the excited leaky guided wave modes is the same as described in commonly owned U.S. patent application Ser. No. 10/765,254, entitled "Leaky Guided Wave Modes Used in Interferometric Confocal Microscopy to Measure Properties of Trenches" (ZI-46) by Henry A. Hill and the contents of which are incorporated herein by reference.

The sensitivity of the change in measured conjugated quadratures to changes in CD' and to depths are measured using independent measurements of the CD's or a simplified inversion analysis. The inversion analysis is simplified as a consequence of the primary measurements being differential. Detailed knowledge of the reflecting properties of two sections that are being compared interferometrically is required when the composition of the two sections are materially different. Because of the high level of modal structure of masks, a detailed knowledge of the mask structure in not required in the location of errors in CD's.

Figure 3:
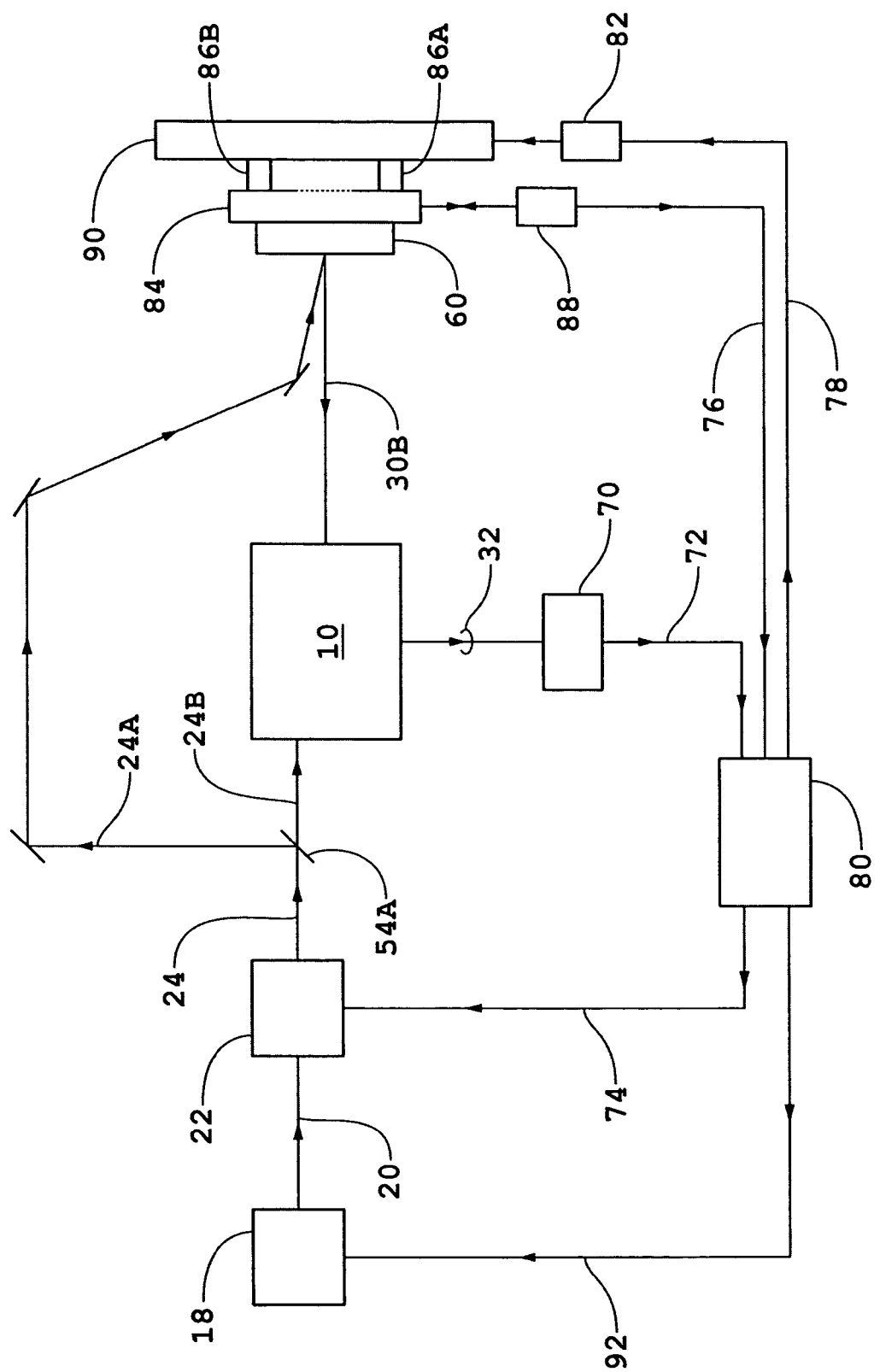
FIG. 3 is a diagram of an interferometric non-confocal microscopy system.

A differential interferometric non-confocal is shown generally in FIG. 3. The description of FIG. 3 is the same as the description given for FIG. 1a except with respect to measurement beam 24A. In FIG. 3, measurement beam 24A is incident on measurement object 60 with an angle of incidence that is nominally zero. The primary difference between the information obtained about the open or filled transparent features using the confocal and non-confocal interferometric microscopy systems is with respect to the properties of the leaky guided wave modes that are excited.

Information is obtained about the horizontal surface of a open or filled transparent feature with a reduced lateral spatial resolution and a reduced depth discrimination of the incident measurement beam for the non-confocal interferometric microscopy system. However, there is an advantage with the non-confocal interferometric microscopy system in that the amplitudes of the excited guided wave modes will generally be larger for the non-confocal interferometric microscopy system as compared to the corresponding confocal system. Another advantage for the non-confocal interferometric microscopy system is that the orders of the excited guided wave modes will generally comprise a smaller set as compared to the corresponding confocal system.

Thus the information obtained about errors in CD's, depths, and the presence of defects in the form of particles from the confocal and the non-confocal interferometric microscopy systems are complimentary and will impact on the selection of one or the other of the confocal or non-confocal systems in an end use application.

In another embodiment, the confocal and non-confocal interferometric microscopy systems are combined in a single interferometric microscopy system. The another embodiment comprises the apparatus of the confocal interferometric microscopy system and a beam delivery system for the measurement beam that switches the measurement beam 24A between a slit-array 114 (see FIGS. 1f and 2c) and to object 60 with a nominal zero angle of incidence.

Other embodiments are described wherein joint measurements are obtained of the conjugated quadratures of fields of complimentary measurement beams reflected/scattered by defects of a measurement object. The complimentary measurement beams correspond to two measurement beams that have orthogonal states of linear polarization. The other embodiments comprise the apparatus of embodiments described in cited U.S. Provisional Patent Application No. 60/459,425 (ZI-50) and U.S. patent application Ser. No. 10/816,180 (ZI-50) and the apparatus and procedures of the first embodiment described herein.

In yet other embodiments, the interferometric metrology systems may be configured in the yet other embodiments to obtain information in the form of joint and non-joint measurements about the angular distribution of the reflected/scattered beams by defects in measurement objects. The yet other embodiments comprise the apparatus described in cited U.S. Provisional Patent Application No. 60/501,666 (ZI-54) and U.S. patent application Ser. No. 10/938,408 (ZI-54) for the acquisition of information about angular distributions.

The interferometric metrology systems described above can be especially useful in alignment mark identification on a stepper or scanner of lithography applications used for fabricating large scale integrated circuits such as computer chips and the like and in a stand-alone metrology system for measuring CD performance of the stepper or scanner. The interferometric metrology systems described above can also be especially useful in inspection of masks used in the stepper or scanner and in the inspection of wafers at different stages of the fabrication of large-scale integrated circuits.

Lithography is the key technology driver for the semiconductor manufacturing industry. In particular, overlay improvement is one of the five most difficult challenges down to and below 100 nm line widths (design rules), see, for example, the *Semiconductor Industry Roadmap*, p 82 (1997). Since a lithography tool may produce $50-100M/year of product, the economic value from improving (maintaining) performance of the lithography tool is substantial. Each 1% increase (loss) in yield of the lithography tool results in approximately $1M/year economic benefit (loss) to the integrated circuit manufacturer and a substantial competitive advantage or disadvantage to the lithography tool vendor.

The function of a lithography tool is to direct spatially patterned radiation onto a photoresist-coated wafer. The process involves determining which location of the wafer is to receive the radiation (alignment) and applying the radiation to the photoresist at that location.

To properly position the wafer, the wafer includes alignment marks on the wafer that can be measured by dedicated sensors such as the interferometric metrology systems described above. The measured positions of the alignment marks define the location of the wafer within the tool. This information, along with a specification of the desired patterning of the wafer surface, guides the alignment of the wafer relative to the spatially patterned radiation. Based on such information, a translatable stage supporting the photoresist-coated wafer moves the wafer such that the radiation will expose the correct location of the wafer.

During exposure, a radiation source illuminates a patterned reticle, which scatters the radiation to produce the spatially patterned radiation. The reticle is also referred to as a mask, and these terms are used interchangeably below. In the case of reduction lithography, a reduction lens collects the scattered radiation and forms a reduced image of the reticle pattern. Alternatively, in the case of proximity printing, the scattered radiation propagates a small distance (typically on the order of microns) before contacting the wafer to produce a 1:1 image of the reticle pattern. The radiation initiates photo-chemical processes in the resist that convert the radiation pattern into a latent image within the resist.

When a mask is made, it must be perfect. Any defects in the pattern will destroy the functionality of the semiconductor circuit that is printed with that mask. Before a mask is delivered to the semiconductor manufacturing line, it is passed through an automated mask inspection system that searches for any defects in the pattern. There are two possible strategies in mask inspection, known as die-to-database and die-to-die inspection. The first method involves an automated scanning microscope or an interferometric metrology system described herein that compares the mask pattern directly with the computer data used to generate the mask. This requires a very large data handling capability, similar to that needed by the mask writer itself. Any discrepancy between the inspected mask pattern and the data set used to create it is flagged as an error. The interferometric metrology systems described above are especially well suited for automated mask inspection with its advantages in background reduction and in the substantially simultaneous acquisition of one-dimensional line section images and two-dimensional section images.

In general, the lithography system, also referred to as an exposure system, typically includes an illumination system and a wafer positioning system. The illumination system includes a radiation source for providing radiation such as ultraviolet, visible, x-ray, electron, or ion radiation, and a reticle or mask for imparting the pattern to the radiation, thereby generating the spatially patterned radiation. In addition, for the case of reduction lithography, the illumination system can include a lens assembly for imaging the spatially patterned radiation onto the wafer. The imaged radiation exposes resist coated onto the wafer. The illumination system also includes a mask stage for supporting the mask and a positioning system for adjusting the position of the mask stage relative to the radiation directed through the mask. The wafer positioning system includes a wafer stage for supporting the wafer and a positioning system for adjusting the position of the wafer stage relative to the imaged radiation. Fabrication of integrated circuits can include multiple exposing steps. For a general reference on lithography, see, for example, J. R. Sheats and B. W. Smith, in *Microlithography: Science and Technology* (Marcel Dekker, Inc., New York, 1998), the contents of which is incorporated herein by reference.

Figure 6A:
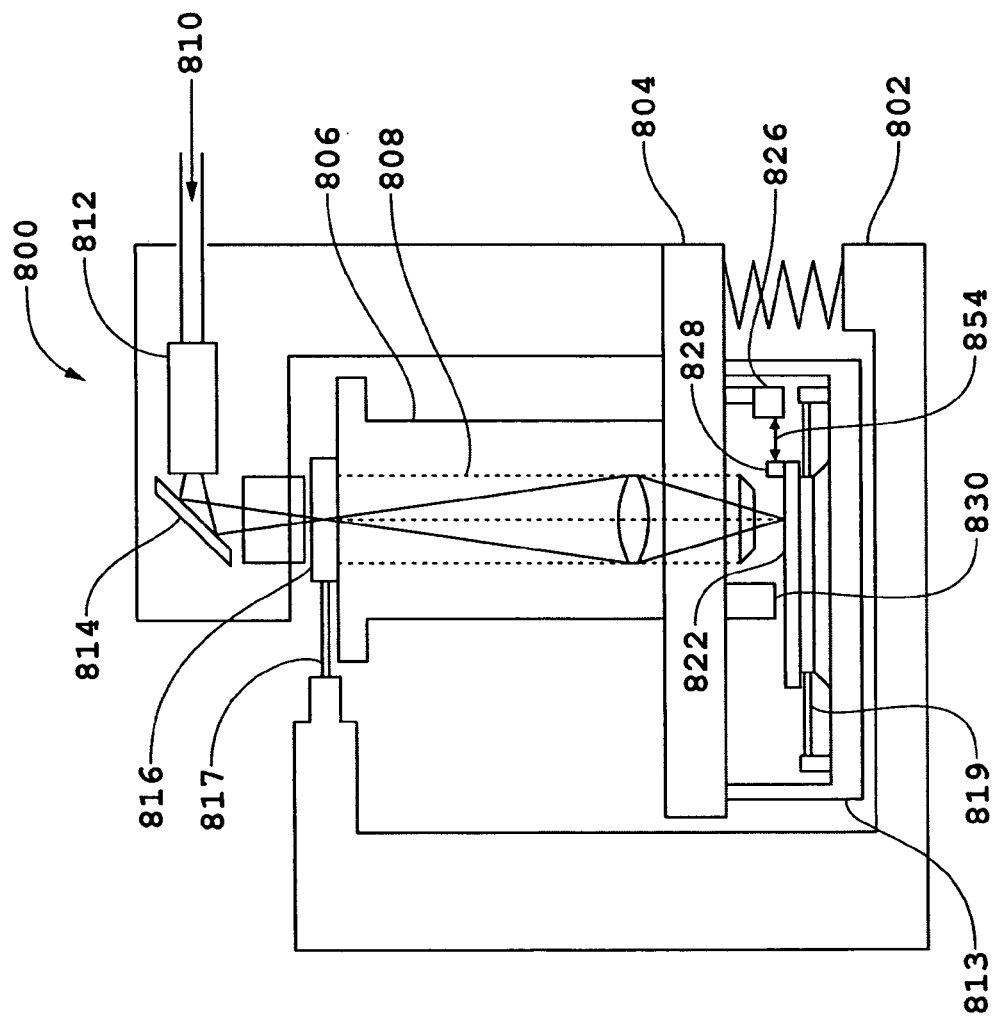
FIG. 6a is a schematic diagram of a lithography tool that uses an interferometric metrology system.

An example of a lithography scanner 800 using an interferometric metrology system 830 is shown in FIG. 6a. Interferometric metrology system 830 is used to precisely locate the position of alignment marks on the wafer (not shown) within an exposure system. Here, stage 822 is used to position and support the wafer relative to an exposure station. Scanner 800 includes a frame 802, which carries other support structures and various components carried on those structures. An exposure base 804 has mounted on top of it a lens housing 806 atop of which is mounted a reticle or mask stage 816, which is used to support a reticle or mask. A positioning system for positioning the mask relative to the exposure station is indicated schematically by element 817. Positioning system 817 can include, e.g., piezoelectric transducer elements and corresponding control electronics. Although, it is not included in this described embodiment, one or more interferometry systems are used to precisely measure the position of the mask stage as well as other moveable elements whose position must be accurately monitored in processes for fabricating lithographic structures (see supra Sheats and Smith *Microlithography: Science and Technology*).

Suspended below exposure base 804 is a support base 813 that carries wafer stage 822. Stage 822 includes a plane mirror 828 for reflecting a measurement beam 854 directed to the stage by interferometry system 826. A positioning system for positioning stage 822 relative to interferometry system 826 is indicated schematically by element 819. Positioning system 819 can include, e.g., piezoelectric transducer elements and corresponding control electronics. The measurement beam reflects back to the interferometry system, which is mounted on exposure base 804.

During operation, a radiation beam 810, e.g., an ultraviolet (UV) beam from a UV laser (not shown), passes through a beam shaping optics assembly 812 and travels downward after reflecting from mirror 814. Thereafter, the radiation beam passes through a mask (not shown) carried by mask stage 816. The mask (not shown) is imaged onto a wafer (not shown) on wafer stage 822 via a lens assembly 808 carried in a lens housing 806. Base 804 and the various components supported by it are isolated from environmental vibrations by a damping system depicted by spring 820.

Interferometric metrology system 830 such as described above is used to locate the position of alignment marks on the wafer and/or the wafer stage 816.

Figure 6B:
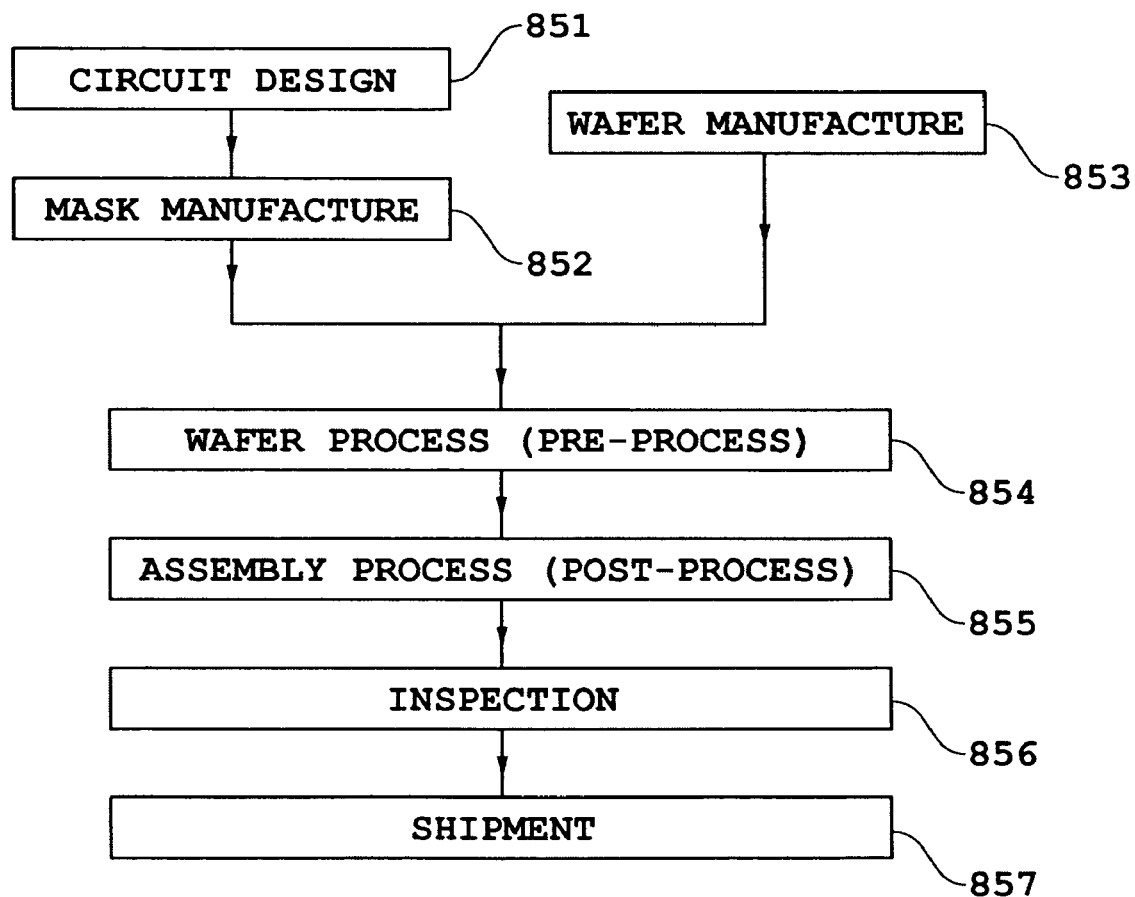
FIG. 6b is a flow chart of the sequence of manufacturing steps of a semiconductor device.

As is well known in the art, lithography is a critical part of manufacturing methods for making semiconductor devices. For example, U.S. Pat. No. 5,483,343 outlines steps for such manufacturing methods. These steps are described below with reference to FIGS. 6b and 6c. FIG. 6b is a flow chart of the sequence of manufacturing a semiconductor device such as a semiconductor chip (e.g. IC or LSI), a liquid crystal panel or a CCD. Step 851 is a design process for designing the circuit of a semiconductor device. Step 852 is a process for manufacturing a mask on the basis of the circuit pattern design. Step 853 is a process for manufacturing a wafer by using a material such as silicon.

Step 854 is a wafer process, which is called a pre-process wherein, by using the so prepared mask and wafer, circuits are formed on the wafer through lithography. To form circuits on the wafer that correspond with sufficient spatial resolution those patterns on the mask, interferometric positioning of the lithography tool relative the wafer is necessary. The catadioptric imaging systems described herein can be especially useful to inspect the surface of the wafer and internal layers generate on the wafer by wafer processing to check and monitor the effectiveness of the lithography used in the wafer process. Step 855 is an assembling step, which is called a post-process wherein the wafer processed by step 854 is formed into semiconductor chips. This step includes assembling (dicing and bonding) and packaging (chip sealing). Step 856 is an inspection step wherein operability check, durability check and so on of the semiconductor devices produced by step 855 are carried out. With these processes, semiconductor devices are finished and they are shipped (step 857).

Figure 6C:
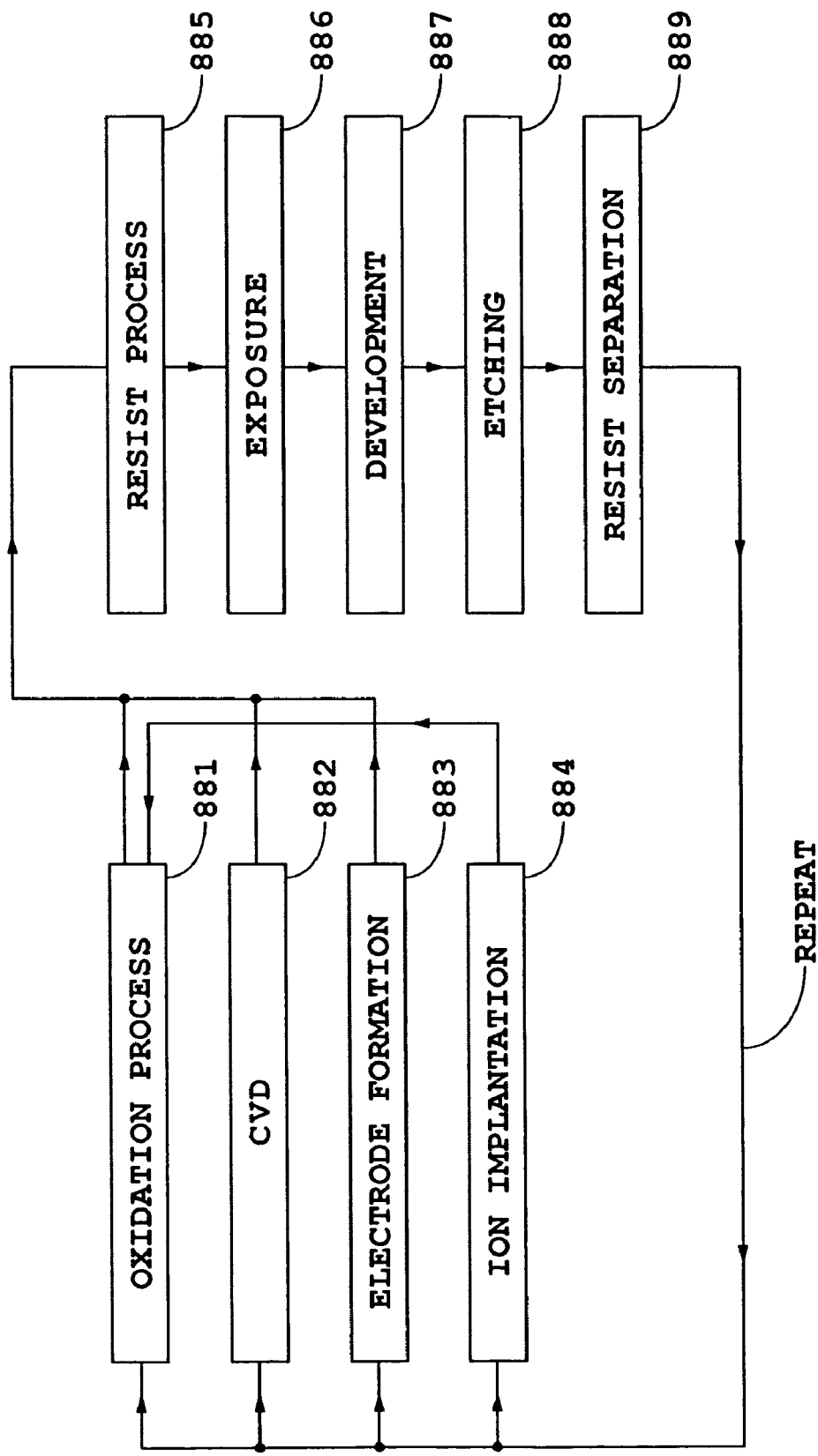
FIG. 6c is a flow chart showing steps of the wafer process.

FIG. 6c is a flow chart showing details of the wafer process. Step 861 is an oxidation process for oxidizing the surface of a wafer. Step 862 is a CVD process for forming an insulating film on the wafer surface. Step 863 is an electrode forming process for forming electrodes on the wafer by vapor deposition. Step 864 is an ion implanting process for implanting ions to the wafer. Step 865 is a resist process for applying a resist (photosensitive material) to the wafer. Step 866 is an exposure process for printing, by exposure (i.e., lithography), the circuit pattern of the mask on the wafer through the exposure apparatus described above. Once again, as described above, the use of the catadioptric imaging systems described herein improve the accuracy, resolution, and maintenance of such lithography steps.

Step 867 is a developing process for developing the exposed wafer. Step 868 is an etching process for removing portions other than the developed resist image. Step 869 is a resist separation process for separating the resist material remaining on the wafer after being subjected to the etching process. By repeating these processes, circuit patterns are formed and superimposed on the wafer.

Figure 7:
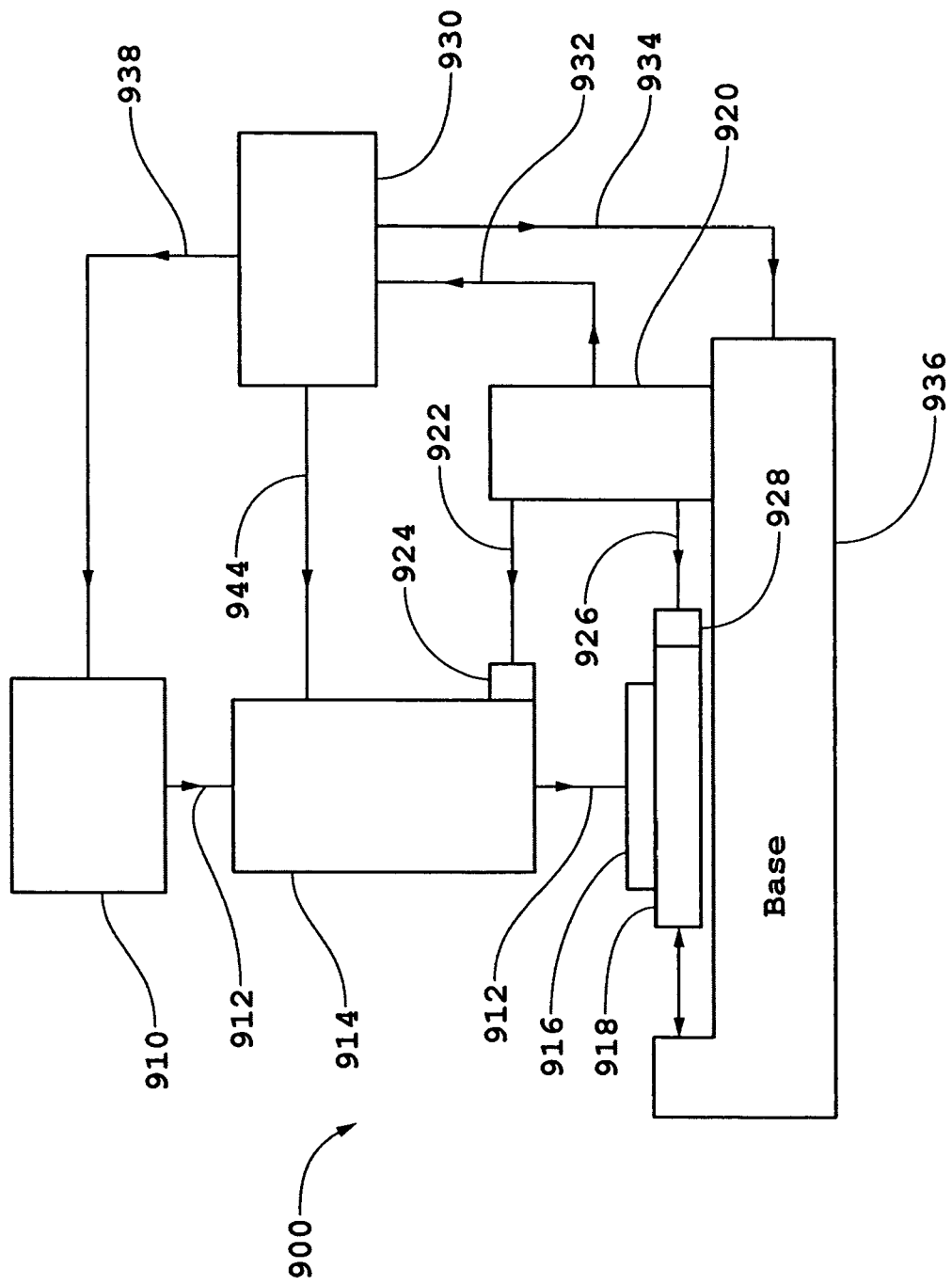
FIG. 7 is a schematic diagram of an inspection tool that uses an interferometric metrology system.

An important application of the interferometric metrology systems described herein is the inspection of patterns on masks and reticles used in the lithography methods described previously, the measurement of CD's on wafers and the inspection of the masks, reticles, and wafers for defects. As an example, a schematic of a mask and wafer inspection system 900 is shown in FIG. 7. A source 910 generates a source beam 912 and an interferometric metrology system 914 such as described herein directs the radiation beam to a substrate 916 supported by a movable stage 918. To determine the relative position of the stage, an interferometry system 920 directs a reference beam 922 to a mirror 924 mounted on beam focusing assembly 914 and a measurement beam 926 to a mirror 928 mounted on stage 918. Changes in the position measured by the interferometry system correspond to changes in the relative position of write beam 912 on substrate 916. Interferometry system 920 sends a measurement signal 932 to controller 930 that is indicative of the relative position of inspection beam 912 on substrate 916. Controller 930 sends an output signal 934 to a base 936 that supports and positions stage 918.

Controller 930 can cause interferometric metrology system assembly 914 to scan the inspection beam over a region of the substrate, e.g., using signal 944. As a result, controller 930 directs the other components of the system to inspect the substrate. The mask and wafer inspection compares the mask, reticle, or wafer pattern obtained with interferometric metrology system 914 directly with computer data used to generate the mask, reticle or the pattern on the wafer.

Other embodiments are within the following claims.

What is claimed is:

1. An interferometry system for examining a surface of an object, said system comprising:
   a source assembly that generates a measurement beam;
   a detector assembly that includes a detector element;
   an interferometer that includes a source imaging system that focuses the measurement beam onto a spot on the surface of the object and an object imaging system that images the spot onto the detector element as an interference beam to generate an interference signal therefrom, said object imaging system combining a return measurement beam coming from the spot with a reference beam to produce the interference beam, wherein the measurement beam upon interaction with the surface of the object produces a backscattered component and a forward-scattered component; and
   a processor programmed to determine oblique angle-of-incidence information about a feature or defect on the surface of the object by using the backscattered component but not the forward scattered component.

2. The interferometry system of claim 1, wherein the object imaging system is configured to collect the backscattered component but not the forward scattered component to generate the return measurement beam.

3. The interferometry system of claim 1, wherein the source imaging system generates the measurement beam such that it has an angle of incidence relative to the surface of the object that ranges between $\theta_1$ and $\theta_2$, wherein $\theta_1$ and $\theta_2$ are angles that are less than 90° and wherein $\theta_1 < \theta_2$.

4. The interferometry system of claim 1, wherein the interferometer is a linear displacement interferometer.

5. The interferometry system of claim 1, wherein the interferometer is a scanning, linear displacement interferometer.

6. The interferometry system of claim 1, further comprising a catadioptric imaging system that implements at least part of both the source imaging system and the object imaging system.

7. An interferometry system for examining a surface of an object, said system comprising:
   a source assembly that generates a measurement beam;
   a detector assembly that includes a detector element; and
   an interferometer that includes a source imaging system that focuses the measurement beam onto a spot on the surface of the object and an object imaging system that images the spot onto the detector element as an interference beam to generate an interference signal therefrom, said object imaging system combining a return measurement beam coming from the spot with a reference beam to produce the interference beam,
   wherein the source imaging system causes the measurement beam that arrives at the surface of the object to have an average angle of incidence that is oblique to the surface of object,
   wherein the measurement beam upon interaction with the surface of the object produces a backscattered component and a forward-scattered component, and
   wherein the object imaging system is configured to collect the backscattered component but not the forward scattered component to generate the return measurement beam.

8. The interferometry system of claim 7, wherein the source imaging system generates the measurement beam such that it has an angle of incidence relative to the surface of the object that ranges between $\theta_1$ and $\theta_2$, wherein $\theta_1$ and $\theta_2$ are angles that are less than 90° and wherein $\theta_1 < \theta_2$.

9. The interferometry system of claim 7, wherein the interferometer is a linear displacement interferometer.

10. The interferometry system of claim 9, wherein the interferometer is a scanning, linear displacement interferometer.

11. The interferometry system of claim 7, further comprising a catadioptric imaging system that implements at least part of both the source imaging system and the object imaging system.

12. An interferometry system for examining a surface of an object, said system comprising:
    a source assembly that generates an array of measurement beams;
    a detector assembly that includes an array of detector elements;
    an interferometer that includes a source imaging system that focuses the array of measurement beams onto an array of spots on the object and an object imaging system that images the array of spots onto the array of detector elements as an array of interference beams, said object imaging system combining an array of return measurement beams coming from the array of spots with an array of reference beams to produce the array of interference beams, wherein the array of measurement beams upon interaction with the surface of the object produces an array of backscattered components and an array of forward-scattered components; and a processor programmed to determine oblique angle-of-incidence information about features or defects on the surface of the object by using the array of backscattered components but not the array of forward scattered components.

13. The interferometry system of claim 12, wherein the source imaging system generates the measurement beam array such that it has an angle of incidence relative to the surface of the object that ranges between $\theta_1$ and $\theta_2$, wherein $\theta_1$ and $\theta_2$ are angles that are less than 90° and wherein $\theta_1 < \theta_2$.

14. The interferometry system of claim 12, wherein the interferometer is a linear displacement interferometer.

15. The interferometry system of claim 14, wherein the interferometer is a scanning, linear displacement interferometer.

16. The interferometry system of claim 12, further comprising a catadioptric imaging system that implements at least part of both the source imaging system and the object imaging system.

17. The interferometry system of claim 12, wherein the source assembly includes an optical component that simultaneously generates a first, a second, and a third array of measurement beams, wherein the first array of measurement beams is said first-mentioned array of measurement beams and said source imaging system causes the first array of measurement beams to arrive at the surface along a first range of directions that is characterized by an average angle of incidence that is oblique to the surface of the object, wherein the source imaging system focuses the second array of measurement beams onto the surface along a second range of directions characterized by an average angle of incidence that is oblique to the surface of the object, said second direction being different from the first direction, and wherein the source imaging system focuses the third array of measurement beams onto the surface so that the third array of measurement beams arrives at the surface of the object with an average angle of incidence that is non-oblique relative to the surface of the object.

18. The interferometry system of claim 17, wherein the source imaging system images the second array of measurement beams onto a second array of spots on the object and images the third array of measurement beams onto a third array of spots on the object, wherein the first, second, and third arrays of spots are distinct from each other.

19. The interferometry system of claim 17, wherein the first and second directions are complimentary to each other.

20. The interferometry system of claim 17, wherein the optical component comprises a pinhole array beam splitter and a spatial filter.

21. An interferometry system for examining a surface of an object, said system comprising:
    a source assembly that generates an array of measurement beams;
    a detector assembly that includes an array of detector elements; and
    an interferometer that includes a source imaging system that focuses the array of measurement beams onto an array of spots on the object and an object imaging system that images the array of spots onto the array of detector elements as an array of interference beams, said object imaging system combining an array of return measurement beams coming from the array of spots with an array of reference beams to produce the array of interference beams,
    wherein the source imaging system causes the array of measurement beams to arrive at the surface along a range of directions that is characterized by an average angle of incidence that is oblique to the surface of the object, wherein the array of measurement beams upon interaction with the surface of the object produces an array of backscattered components and an array of forward-scattered components and wherein the object imaging system uses the array of backscattered components but not the array of forward scattered components to generate the array of return measurement beams.

22. The interferometry system of claim 21, wherein the source imaging system generates the measurement beam array such that it has an angle of incidence relative to the surface of the object that ranges between $\theta_1$ and $\theta_2$, wherein $\theta_1$ and $\theta_2$ are angles that are less than 90° and wherein $\theta_1 < \theta_2$.

23. The interferometry system of claim 21, wherein the interferometer is a linear displacement interferometer.

24. The interferometry system of claim 23, wherein the interferometer is a scanning, linear displacement interferometer.

25. The interferometry system of claim 21, further comprising a catadioptric imaging system that implements at least part of both the source imaging system and the object imaging system.

26. The interferometry system of claim 21, wherein the source assembly includes an optical component that simultaneously generates a first, a second, and a third array of measurement beams, wherein the first array of measurement beams is said first-mentioned array of measurement beams, wherein the source imaging system focuses the second array of measurement beams onto the surface along a second range of directions characterized by an average angle of incidence that is oblique to the surface of the object, said second direction being different from the first-mentioned direction, and wherein the source imaging system focuses the third array of measurement beams onto the surface so that the third array of measurement beams arrives at the surface of the object with an average angle of incidence that is non-oblique relative to the surface of the object.

27. The interferometry system of claim 26, wherein the source imaging system images the second array of measurement beams onto a second array of spots on the object and images the third array of measurement beams onto a third array of spots on the object, wherein the first, second, and third arrays of spots are distinct from each other.

28. The interferometry system of claim 26, wherein the first and second directions are complimentary to each other.

29. The interferometry system of claim 26, wherein the optical component comprises a pinhole array beam splitter and a spatial filter.

30. A method of interferometrically examining a surface of an object, said method comprising:
generating a measurement beam;
focusing the measurement beam onto a spot on the surface of the object wherein upon interaction with the surface of the object the measurement beam produces a backscattered component and a forward-scattered component;
combining a return measurement beam from the object with a reference beam to generate an interference beam;
generating an interference signal from the interference beam; and
from the interference signal, determining oblique angle-of-incidence information about a feature or defect on the surface of the object, wherein determining involves using the backscattered component but not the forward scattered component.

31. The method of claim 30, further comprising collecting the backscattered component from the surface of the object but not the forward scattered component to generate the return measurement beam.

32. The method of claim 30, further comprising interferometrically determining height profile information about the surface of the object.

33. The method of claim 32, further comprising using both the height profile information and the oblique angle-of-incidence information to determine locations of features on the surface of the object.

34. A method of interferometrically examining a surface of an object, said method comprising:
generating an array of measurement beams;
focusing the array of measurement beams onto an array of spots on the object, wherein upon interacting with the surface of the object the array of measurement beams produces an array of backscattered components and an array of forward-scattered components;
combining an array of return measurement beams from the object with an array of reference beams to generate an array of interference beams;
generating an array of interference signals form the array of interference beams;
from the array of interference signals, determining oblique angle-of-incidence information about a feature or defect on the surface of the object, wherein determining involves using the array of backscattered components but not the array forward scattered components.

35. The method of claim 34, wherein focusing the first-mentioned array of measurement beams onto the object involves delivering the first-mentioned array of measurement beams onto the object along a first range of directions characterized by an average angle of incidence that is oblique to the surface of the object, said method further comprising:
generating a second array of measurement beams;
focusing the second array of measurement beams onto the object so that the second array of measurement beams arrives at the surface along a second range of directions characterized by an average angle of incidence that is non-oblique to the surface of the object.

36. The method of claim 35, wherein upon interacting with the surface of the object the second array of measurement beams produces a second array of return measurement beams, said method further comprising:
combining the second array of return measurement beams from the object with a second array of reference beams to generate a second array of interference beams; and
from the second array of interference signals, determining height profile information about the surface of the object.

37. The method of claim 36, further comprising using both the height profile information and the oblique angle-of-incidence information to determine locations of features on the surface of the object.

38. The method of claim 37, wherein generating and focusing of the first and second arrays of measurement beams takes place concurrently.

39. The method of claim 38, further comprising scanning the first and second arrays of measurement beams across the surface of the object.

* * * * *